(12) United States Patent
Williamson, IV et al.

(10) Patent No.: US 7,326,177 B2
(45) Date of Patent: Feb. 5, 2008

(54) TISSUE STABILIZER HAVING AN ARTICULATING LIFT ELEMENT

(75) Inventors: William P. Williamson, IV, Loveland, OH (US); Paul A. Spence, Louisville, KY (US); Mark Ortiz, Milford, OH (US); George A. Keller, Grandview Heights, OH (US); Harry Leonard Green, II, Santa Cruz, CA (US)

(73) Assignee: Cardiothoracic Systems, Inc.

( * ) Notice: Subject to any disclaimer, the term of this patent is extended or adjusted under 35 U.S.C. 154(b) by 412 days.

(21) Appl. No.: 10/137,643

(22) Filed: Apr. 30, 2002

(65) Prior Publication Data

US 2002/0165434 A1 Nov. 7, 2002

Related U.S. Application Data

(63) Continuation of application No. 09/398,535, filed on Sep. 16, 1999, now Pat. No. 6,406,424.

(51) Int. Cl.
*A61B 1/32* (2006.01)
*A61F 2/00* (2006.01)

(52) U.S. Cl. .................. 600/201; 600/205; 600/37
(58) Field of Classification Search ............ 600/199, 600/201, 205, 206, 210, 235, 232, 214, 215, 600/222, 37, 217; 269/21, 22; 601/6, 113, 601/7–14; 128/898; 606/123, 124, 115
See application file for complete search history.

(56) References Cited

U.S. PATENT DOCUMENTS

| 452,131 | A | 5/1891 | Haughawout |
|---|---|---|---|
| 810,675 | A | 1/1906 | Richter |
| 1,706,500 | A | 3/1929 | Smith |
| 2,296,793 | A | 9/1942 | Kirschbaum |
| 2,590,527 | A | 3/1952 | Fluck |

(Continued)

FOREIGN PATENT DOCUMENTS

AU 713601 3/2000

(Continued)

OTHER PUBLICATIONS

U.S. Appl. No. 09/345,859, filed Jul. 1, 1999, Looney et al.

(Continued)

*Primary Examiner*—Julian W. Woo
(74) *Attorney, Agent, or Firm*—Law Office of Alan W. Cannon

(57) ABSTRACT

Devices and methods are disclosed for stabilizing tissue within a patient's body during a surgical operation to provide a relatively motionless surgical field, such as during a coronary artery bypass graft procedure. The devices include tissue stabilizers which engage and provide stabilization to a targeted area of tissue and further have the ability to engage and manipulate some portion of tissue within or adjacent the targeted area to improve the surgical presentation of that portion of tissue. The tissue stabilizer typically has one or more stabilizer feet which have a first foot portion configured to provide stabilization to the targeted tissue and a second foot portion moveable relative to the first foot portion for manipulating a portion of tissue to improve the surgical presentation.

23 Claims, 9 Drawing Sheets

U.S. PATENT DOCUMENTS

| | | |
|---|---|---|
| 2,693,795 A | 11/1954 | Grieshaber |
| 2,863,444 A | 12/1958 | Winsten |
| 3,392,722 A | 7/1968 | Jorgensen |
| 3,584,822 A | 6/1971 | Oram |
| 3,683,926 A | 8/1972 | Suzuki |
| 3,720,433 A | 3/1973 | Rosfelder |
| 3,783,873 A | 1/1974 | Jacobs |
| 3,858,926 A | 1/1975 | Ottenhucs |
| 3,882,855 A | 5/1975 | Schulte et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,052,980 A | 10/1977 | Grams et al. |
| 4,217,890 A | 8/1980 | Owens |
| 4,226,228 A * | 10/1980 | Shin et al. .................. 600/206 |
| 4,230,119 A | 10/1980 | Blum |
| 4,306,561 A | 12/1981 | de Medinaceli |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,925,443 A | 5/1990 | Heilman et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundbach |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,119,804 A | 6/1992 | Anstadt |
| 5,125,395 A | 6/1992 | Adair |
| 5,131,905 A | 7/1992 | Grooters et al. |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,196,003 A | 3/1993 | Bilweis |
| 5,231,974 A | 8/1993 | Giglio et al. |
| 5,256,132 A | 10/1993 | Snyders |
| 5,287,861 A | 2/1994 | Wilk |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cohen |
| 5,348,259 A | 9/1994 | Blanco et al. |
| 5,363,882 A | 11/1994 | Chikama |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,453,078 A | 9/1995 | Valentine et al. |
| 5,467,763 A | 11/1995 | McMahon et al. |
| 5,480,425 A | 1/1996 | Ogilive |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,522,819 A | 6/1996 | Graves et al. |
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,582,580 A | 12/1996 | Buckman, Jr. et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,632,746 A | 5/1997 | Middleman et al. |
| 5,651,378 A | 7/1997 | Matheny et al. |
| 5,662,300 A | 9/1997 | Michelson |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |
| 5,795,291 A | 8/1998 | Koros et al. |
| 5,797,960 A | 8/1998 | Stevens et al. |
| 5,799,661 A | 9/1998 | Boyd et al. |
| 5,807,243 A | 9/1998 | Vierra et al. |
| 5,813,410 A | 9/1998 | Levin |
| 5,836,311 A * | 11/1998 | Borst et al. .................. 600/201 |
| 5,846,187 A | 12/1998 | Wells et al. |
| 5,846,193 A | 12/1998 | Wright |
| 5,846,194 A | 12/1998 | Wasson et al. |
| 5,865,730 A | 2/1999 | Fox et al. |

| | | |
|---|---|---|
| 5,868,770 A | 2/1999 | Rygaard |
| 5,875,782 A | 3/1999 | Ferrari et al. |
| 5,876,332 A | 3/1999 | Looney |
| 5,879,291 A | 3/1999 | Kolata et al. |
| 5,882,299 A | 3/1999 | Rastegar et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A | 5/1999 | Corey, Jr. et al. |
| 5,906,607 A | 5/1999 | Taylor et al. |
| 5,908,382 A | 6/1999 | Koros et al. |
| 5,913,876 A | 6/1999 | Taylor et al. |
| 5,927,284 A | 7/1999 | Borst et al. |
| 5,944,658 A | 8/1999 | Koros et al. |
| 5,944,736 A | 8/1999 | Taylor et al. |
| 5,947,125 A | 9/1999 | Benetti |
| 5,947,896 A | 9/1999 | Sherts et al. |
| 5,957,835 A | 9/1999 | Anderson et al. |
| 5,961,481 A | 10/1999 | Sterman et al. |
| 5,967,972 A | 10/1999 | Santilli et al. |
| 5,967,973 A | 10/1999 | Sherts et al. |
| 5,976,080 A | 11/1999 | Farascioni |
| 5,976,171 A | 11/1999 | Taylor |
| 5,984,864 A | 11/1999 | Fox et al. |
| 5,984,865 A | 11/1999 | Farley et al. |
| 5,984,867 A | 11/1999 | Deckman et al. |
| 6,007,486 A | 12/1999 | Hunt et al. |
| 6,007,523 A | 12/1999 | Mangosong |
| 6,010,531 A | 1/2000 | Donlon et al. |
| 6,013,027 A | 1/2000 | Khan et al. |
| 6,015,378 A | 1/2000 | Borst et al. |
| 6,015,427 A | 1/2000 | Mueller et al. |
| 6,017,304 A | 1/2000 | Vierra et al. |
| 6,019,722 A | 2/2000 | Spence et al. |
| 6,027,476 A | 2/2000 | Sterman et al. |
| 6,029,671 A | 2/2000 | Stevens et al. |
| 6,030,340 A | 2/2000 | Maffei et al. |
| D421,803 S | 3/2000 | Koros et al. |
| 6,032,672 A | 3/2000 | Taylor |
| 6,033,362 A | 3/2000 | Cohn |
| 6,036,641 A | 3/2000 | Taylor et al. |
| 6,050,266 A | 4/2000 | Benetti et al. |
| 6,063,021 A | 5/2000 | Hossain et al. |
| 6,071,295 A | 6/2000 | Takahashi |
| 6,074,343 A * | 6/2000 | Nathanson et al. ......... 600/214 |
| 6,099,468 A | 8/2000 | Santilli et al. |
| 6,102,853 A | 8/2000 | Scirica et al. |
| 6,102,854 A | 8/2000 | Carfier et al. |
| 6,139,492 A | 10/2000 | Vierra et al. |
| 6,149,583 A | 11/2000 | Vierra et al. |
| 6,152,874 A * | 11/2000 | Looney et al. .............. 600/214 |
| 6,167,889 B1 | 1/2001 | Benetti |
| 6,183,486 B1 | 2/2001 | Snow et al. |
| 6,190,311 B1 | 2/2001 | Glines et al. |
| 6,193,652 B1 | 2/2001 | Berky et al. |
| 6,193,732 B1 | 2/2001 | Frantzen et al. |
| 6,196,982 B1 | 3/2001 | Ball |
| 6,200,263 B1 | 3/2001 | Person |
| 6,210,323 B1 | 4/2001 | Gilhuly et al. |
| 6,213,940 B1 | 4/2001 | Sherts et al. |
| 6,213,941 B1 | 4/2001 | Benetti et al. |
| 6,231,506 B1 * | 5/2001 | Hu et al. .................... 600/210 |
| 6,251,065 B1 * | 6/2001 | Kochamba et al. ........... 600/37 |
| 6,283,912 B1 | 9/2001 | Hu et al. |
| 6,290,644 B1 | 9/2001 | Green, II et al. |
| 6,328,688 B1 | 12/2001 | Borst et al. |
| 6,331,158 B1 | 12/2001 | Hu et al. |
| 6,334,843 B1 | 1/2002 | Borst et al. |
| 6,336,898 B1 | 1/2002 | Borst et al. |
| 6,346,077 B1 | 2/2002 | Taylor et al. |
| 6,350,229 B1 | 2/2002 | Borst et al. |
| 6,364,826 B1 | 4/2002 | Borst et al. |
| 6,371,906 B1 | 4/2002 | Borst et al. |
| 6,394,948 B1 | 5/2002 | Borst et al. |
| 6,406,424 B1 | 6/2002 | Williamson, IV et al. |
| 6,464,629 B1 | 10/2002 | Boone et al. |
| 6,464,630 B1 | 10/2002 | Borst et al. |
| 6,740,028 B2 | 5/2004 | Boone et al. |
| 6,755,780 B2 | 6/2004 | Borst et al. |

FOREIGN PATENT DOCUMENTS

| | | |
|---|---|---|
| CA | 2197608 | 2/2000 |
| DE | 31 38 589 A1 | 4/1983 |
| DE | 90 04513 | 6/1990 |
| DE | 41 39 695 A1 | 6/1993 |
| EP | 0 293 760 A2 | 12/1988 |
| EP | 0 293 760 A3 | 12/1988 |
| EP | 0 293 760 B1 | 12/1988 |
| EP | 0 630 629 A1 | 5/1994 |
| EP | 668 058 A1 | 8/1995 |
| EP | 0791 330 A2 | 8/1997 |
| EP | 0 803 228 A1 | 10/1997 |
| EP | 0 808 606 A1 | 11/1997 |
| EP | 0 919 193 A1 | 6/1999 |
| EP | 0 993 806 A2 | 4/2000 |
| FR | 473451 | 1/1915 |
| GB | 168216 | 9/1921 |
| GB | 2 233 561 A | 1/1991 |
| GB | 2 267 827 A | 12/1993 |
| SU | 938967 | 7/1982 |
| WO | WO 87/04081 | 7/1987 |
| WO | WO 88/00481 | 1/1988 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/26828 | 7/1997 |
| WO | WO 97/32514 A2 | 9/1997 |
| WO | WO 97/32514 A3 | 9/1997 |
| WO | WO 97/40752 | 11/1997 |
| WO | WO 98/27869 | 7/1998 |
| WO | WO 98/48703 | 11/1998 |
| WO | WO 98/49944 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

U.S. Appl. No. 09/438,670, filed Nov. 12, 1999, Parsons et al.
U.S. Appl. No. 09/489,274, filed Jan. 21, 2000, Brown et al.
U.S. Appl. No. 60/117,333, filed Jan. 24, 1999, Looney et al.
Akins, et al., "*Preservation of Interventricular Septal Function in Patients Having Coronary Artery Bypass Graft Without Cardiopulmonary Bypass,*" American Heart Journal, vol. 107, No. 2, Feb., 1984, pp. 304-309.
Ancalmo, N. and J. L. Ochsner: "*A Modified Sternal Retractor,*" Ann. Thorac, Surg. 21 (1976) 174.
Angelini, G.D., M.D. et al., "*Fiber-Optic Retractor for Harvesting the Internal Mammary Artery,*" Ann. Thorac. Surg. (1990; 50:314-5).
Angelini, G.D., M.D., (1988) "*Simple, Inexpensive Method of Heart Retraction During Coronary Artery Bypass Surgery,*" Ann. Thora. Surg 46:46-247.

Ankeney (1975) "To use or not to use the pump oxygenator in coronary bypass operations." *Ann. Thorac Surg.*, vol. 19(1):108-9.

Anstadt, M.D., et al., "*Direct Mechanical Ventricular Actuation for Cardiac Arrest in Humans,* " Chest, vol. 100, No. 1, Jul. 1991.

Antinori, C. et al., "*A Method of Retraction During Reoperative Coronary Operations Using the Favaloro Retractor,* "The Society of Thoracic Surgeons: 1989.

Archer, Do, et al., "*Coronary Artery Revascularization Without Cardiopulmonary Bypass,*" Texas Heart Institute Journal, vol. 11, No. 1, Mar. 1984, pp. 52-57.

Arom, K.V., et al., "Mini-Sternotomy for Coronary Artery Bypass Grafting," The Annals of Thoracic Surgery 1996; 61:1271-2.

Ballantyne, M.D., et al., "*Delayed Recovery of Severally 'Stunned' Myocardium with the Support of a Left Ventricular Assist Device After Coronary Artery Bypass Graft Surgery,*" Journal of the American College of Cardiology, vol. 10, No. 3, Sep. 1987, pp. 710-712.

Bedellino, M.M., et al., "*The Cardiac Rag—Simple Exposure of the Heart,*" Texas Heart Institute Journal, vol. 15, No. 2, 1988, 134-35.

Beg, R.A., et al., "*Internal Mammary Retractor,*" Ann Thorac, Surg., vol. 39, No. 1, pp. 286-287, Jan. 1985.

Benetti, et al., "*Direct Coronary Surgery with Saphenous Vein Bypass Without Either Cardiopulmonary Bypass or Cardiac Arrest,*" The Journal of Cardiovascular Surgery, vol. 26, No. 3, May-Jun., 1985, pp. 217-222.

Benetti, et al., "*Direct Myocardial Revascularization Without Extracorporeal Circulation,* " Chest, vol. 100, No. 2 Aug. 1991, pp. 312-316.

Benetti et al. (1995) "Coronary Revascularization with Arterial Conduits via a Small Thoracotomy and Assisted by Thoracoscopy, Although without Cardiopulmonary Bypass." *Cor Europaeum*, vol. 4(1):22-24.

Bonatti, J., et al., "*A Single Coronary Artery Bypass Grafting—A Comparison Between Minimally Invasive Off Pump Techniques and Conventional Procedures,*" European Journal of Cardio-Thoracic Surgery, 14 (Supp. I) (1998) S7-S12.

Borst, et al., "*Coronary Artery Bypass Grafting Without Cardiopulmonary Bypass and Without Interruption of Native Coronary Flow Using a Novel Anastomosis Site Restraining Device ("Octopus"),* " J Am Coll Cardiol, May 1996, vol. 27, No. 6, pp. 1356-1364.

Borst, et al., "*Regional Cardiac Wall Immunobilization for Open Chest and Closed Chest Coronary Artery Bypass Grafting on the Beating Heart; 'Octopus' Method,* " Circulation, Oct. 15, 1995, vol. 92, No. 8, supplement 1, 1-177.

Buffolo, et al., "*Direct Myocardial Revascularization Without Cardiopulmonary Bypass,* " Thoac. Cardiovasc. Surgeon, 33 (1985) pp. 26-29.

Bugge, M., "*A New Internal Mammary Artery Retractor,* " Thorac. Cardiovasc Surgeon 38, pp. 316-317 (1990).

Calafiore, A. M., et al., "*Minimally Invasive Coronary Artery Bypass Grafting,*" The Annals of Thoracic Surgery, 62:1545-8, 1996.

Calvin (1990) "Circumflex Exposure Using a Cardiac Sling." Ann Thorac Surg., vol. 49:833-4.

Campalani et al., (1987) "A New Self-Retaining Internal mammary Artery Retractor." *J. Cardiovas. Surg.*, vol. 28.

Cartier, R, MD., "*Triple Coronary Artery Revascularization on the Stabilized Beating Heart: Initial Experience,*" Montreal Heart Institute, CJS, vol. 41, No. 4, pp. 283-288, Aug. 1998.

Chaux, A. and C. Blanche, "*A New Concept in Sternal Retraction: Applications for Internal Mammary Artery Dissection and Valve Replacement Surgery,*" Ann. Thorac. Surg. 42, pp. 473-474, Oct. 1986.

Cohen et al. (1996) "Mini-Sternotomy for Coronary Artery Bypass Grafting *To the Editor:*" Ann. *Thorac. Surg.*, vol. 62:1883-92.

Cooley, D. A., "*Limited Access Myocardial Revascularization,*" Texas Heart Institute Journal, pp. 81-84, vol. 23, No. 2, 1996.

Cremer, J, MD, "*Off-Bypass Coronary Bypass Grafting Via Minithoracotomy Using Mechanical Epicardial Stabilization,*" The Annals of Thoracic Surgery, 63:S79-83, 1997.

Cutler et al. (1980) "New Use for an Old Clamp." *Arch Surg.*, vol. 115:1136-1137.

Delacroix-Chevalier Surgical Instruments, IMA Saving Packages Brochure.

DelRossi, A J and Lemole, GM, "*A New Retractor to Aid in Coronary Artery Surgery,* " The Annals of Thoracic Surgery, vol. 36, No. 1, 101-102, Jul. 1983.

Eguchi (1987) "A Special Retracter for Stabilizing the Heart During Circumflex Coronary Grafting." *Kyobu Geka*, vol. 40(1):39-40.

Fanning, MD., "*Reoperative Coronary Artery Bypass Grafting Without Cardiopulmonary Bypass,* " The Annals of Thoracic Surgery, vol. 55, No. 2, Feb. 1993, pp. 486-489.

Favaloro, M.D., et al, "*Direct Myocardial Revascularization by Saphenous Vein Graft,* " The Annals of Thoracic Surgery, vol. 10, No. 2, Aug. 1970.

Fonger, et al., "*Enhanced Preservation of Acutely Ischemic Myocardium with Transeptal Left Ventricular Assist,*" The Annals of Thoracic Surgery, vol. 57, No. 3, Mar. 1994, pp. 570-575.

Gacioch, et al., "*Cardiogenic Shock Complicating Acute Myocardial Infarction: The Use of Coronary Angioplasty and the Integracion of the New Support Device into Patient Management,*" Journal of the American College of Cardiology, vol. 19, No. 3, Mar. 1, 1992.

Green, GE., "*Technique of Internal Mammary-Coronary Artery Anastomosis,*" The Journal of Cardiovascular Surgery, 78:455-79, 1979.

Groopman, J., "*Heart Surgery, Unplugged; Making the Coronary Bypass Safer, Cheaper, and Easier,*" The New Yorker, Jan. 11, 1999, pp. 43-46, 50-51.

Guzman, F. M.D., "*Transient Radial Nerve Injury Related to the Use of A Self Retraining Retractor for Internal Mammary Artery Dissection,*" J. Cardiovasc. Surg. 30, 1989, pp. 1015-1016.

Hasan, RI, et al., "Technique of Dissecting the Internal Mammary After Using the Moussalli Bar," European Journal of Cardiothoracic Surgery, 4:571-572, 1990.

Itoh, Toshiaki, M.D., et al., "*New Modification of a Mammary Artery Retractor,*" Ann. Thorac. Surg. 9, 1994; 57:1670-1.

Izzat, FRCS, et al., "*Cardiac Stabilizer for Minimally Invasive Direct Coronary Artery Bypass,* " Elsevier Science Inc., 1997 by the Society of Thoracic Surgeons.

Janke "Heart Support for Coronary Bypass Surgery Involving the Circumflex Artery System." *The Journal of Thoracic and Cardiovascular Surgery*, vol. 67(6):883-4.

Japanese Article "*Heart Retractor*".

Japanese Journal of Thoracic Surgery, vol. 42, No. 2, 1989.

Kazama, S. et al., "*Fabric Heart Retractor for Coronary Artery Bypass Operations,*" The Annals of Thoracic Surgery, 55:1582-3, 1993.

Kolessov, M.D., "*Mammary Artery-Coronary Artery Anastomosis as Method of Treatment for Angina Pectoris,*" Thoracic and Cardiovascular Surgery, vol. 54, No. 4, Oct., 1967, pp. 535-544.

Konishi, T. MD, et al., "*Hybrid-Type Stabilizer for Off-Pump Direct Coronary Artery Bypass Grafting,*" Annals of Thoracic Surgery 66:961-2, 1998.

Kresh, et al., "*Heart-Mechanical Assist Device Interaction,* " Trans. Am. Soc. Artif. Intern. Organs, vol. XXXII, 1986, pp. 437-443.

Lavergne, et al., "*Transcatheter Radiofrequency Ablation of Atrial Tissue Using a Suction Catheter,*" PACE, vol. 12, Jan. 1989, Part II, pp. 177-186.

Lonn, M.D., et al. "*Coronary Artery Operation Supported by the Hemopump: An Experimental Study on Pigs,*" The Annals of Thoracic Surgery, vol. 58, No. 1, Jul. 1994, pp. 516-523.

Matsuura, A. MD, et al., "*A New Device for Exposing the Circumflex Coronary Artery,*" The Annals of Thoracic Surgery, 59:1249-50, 1995, pp. 1249-1250.

McGee, et al. "*Extended Clinical Support with an Implatnable Left Ventricular Assist Device,* " Trans. Am Soc. Artif. Intern. Organs, vol. XXXV, 1989, pp. 614-616.

McKeown, P.P. et al., (1981) "*A Modified Sternal Retractor for Exposure of the Internal Mammary Artery,*" Ann. Thorac. Surg. 32: 619.

Ochsner, JL, et al., "*Surgical Management of Diseased Intracavitary Coronary Arteries,*" The Annals of Thoracic Surgery, vol. 38, No. 4, Jul., pp. 356-362, Oct. 1984.

Parsonnet, V. MD, et al., "*Graduated probes for Coronary Bypass Surgery*," The Journal of Thoracic and Cardiovascular Surgery, vol. 68, No. 3, 424-26 (Sep. 1974).

Parsonnet, V. MD, et al., "*Self-Retaining Epicardial Retractor for Aortocoronary Bypass Surgery*," The Journal of Thoracic and Cardiovascular Surgery, 629-30 1979.

Perrault, L. et al., "*Snaring of the Target Vessel in Less Invasive Bypass Operations Does Not Cause Endothelial Dysfunction*," The Society of Thoracic Surgeons, pp. 751-755, 1997.

Pfister, et al., "*Coronary Artery Bypass Without Cardiopulmonary Bypass,*" The Annals of Thoracic Surgery, vol. 54, No. 6, Dec. 1992, pp. 1085-1092.

Phillips, Steven J., M.D. et al., "*A Versatile Retractor for Use in Harvesting the Internal Mammary Artery and Performing Standard Cardiac Operations*," J. Thorac. Cardiovasc. Surg. (1989; 97:633-5).

Pilling Surgical Instruments, A Rusch International Company Brochure.

Pittman, John, M.D., et al., "*Improved Visualization of the Internal Mammary Artery with a New Retractor System*," Ann. Thorac. Surg., 1989; 48:869-70.

Riahi, et al., "*A Simple Technique and Device to Provide a Bloodless Operative Field in Coronary Artery Surgery Without Cross-Clamping the Aorta,*" The Journal of Thoracic and Cardiovascular Surgery, vol. 66, No. 6., Dec. 1973, pp. 974-978.

Richenbacher, M.D., et al., "*Current Status of Cardiac Surgery: A 40-Year Review,*" Journal of American College of Cardiology, vol. 14, No. 3, pp. 535-544.

Robicsek, F., "*Aortic Spoon-Jaw Clamp for Aorta-Saphenous Vein Anastomosis*," Journal of Cardiac Surgery, 10:583-585, 1995.

Robinson, et al., "*A Minimally Invasive Surgical Method for Coronary Revascularization—Preliminary Experience in Five Patients,*" Circulation, Oct. 15, 1995, vol. 92, No. 8, 1-176.

Rousou, J. et al., "*Cardiac Retractor for Coronary Bypass Operations*," The Society of Thoracic Surgeons, pp. 52:877-78, 1991.

Roux, D. MD. et al., "*New Helper Instrument in Cardiac Surgery*," The Annals of Thoracic Surgery, 48: 595-6, 1989.

Roux, D., M.D. et al., "*Internal Mammary Artery Dissection: A Three Dimensional Sternal Retractor*," J. Cardiovasc. Surg., 1989; 30:996-7.

Ruzevich et al. "*Long-Term Follow-up of Survivors of Postcardiotomy Circulatory Support,*"Trans. Am. Soc. Artif. Intern. Organs, vol. XXXIV, 1988, pp. 116-124.

Scholz, et al. "*Transfemoral Placement of the Left Ventricular Assist Device 'Hemopump' During Mechanical Resuscitation*,"Thoracic and Cardiovascular Surgeon, vol. 38 (1990) pp. 69-72.

Splittgerber et al. (1996) "Exposing the Circumflex Coronary Artery: The Heartflip Technique." *Ann Thorac Surg.*, vol. 61:1019-20.

Stevens, et al., "*Closed Chest Coronary Artery Bypass With Cardioplegic Arrest in the Dog,*" $67^{th}$ Scientific Session, 238, I-251.

Trapp, et al., "*Placement of Coronary Artery Bypass Graft without Pump Oxygenator,*" Journal of the Society of Thoracic Surgeons and The Southern Thoracic Surgeons Assn. vol. 19, No. 1, Jan. 1975.

USSC Cardiovascular Thora-Lift J, United States Surgical Corporation, Norwalk, Connecticut, Product Brochure.

Vigano, M., "*Tecnica Operatoria*," Minerva Cardioangiologica, vol. 23-N. 6-7 (1975).

Vincent, J.G., "*A Compact Single Post Internal Mammary Artery Dissection Retractor*," Eur. J. Cardio-Thor. Surg. 3 (1989) 276-277.

Westaby (1995) "Coronary Surgery without Cardiopulmonary Bypass." *British Heart Journal*, vol. 73:203-205.

Westaby, S. et al., "*Less Invasive Coronary Surgery: Consensus From the Oxford Meeting*," The Annals of Thoracic Surgery, 62:924-31, 1996.

Zumbro, et al., "*A Prospective Evaluation of the Pulsatile Assist Device*," The Annals of Thoracic Surgery, vol. 28, No. 2, Aug. 1979, pp. 269-273.

\* cited by examiner

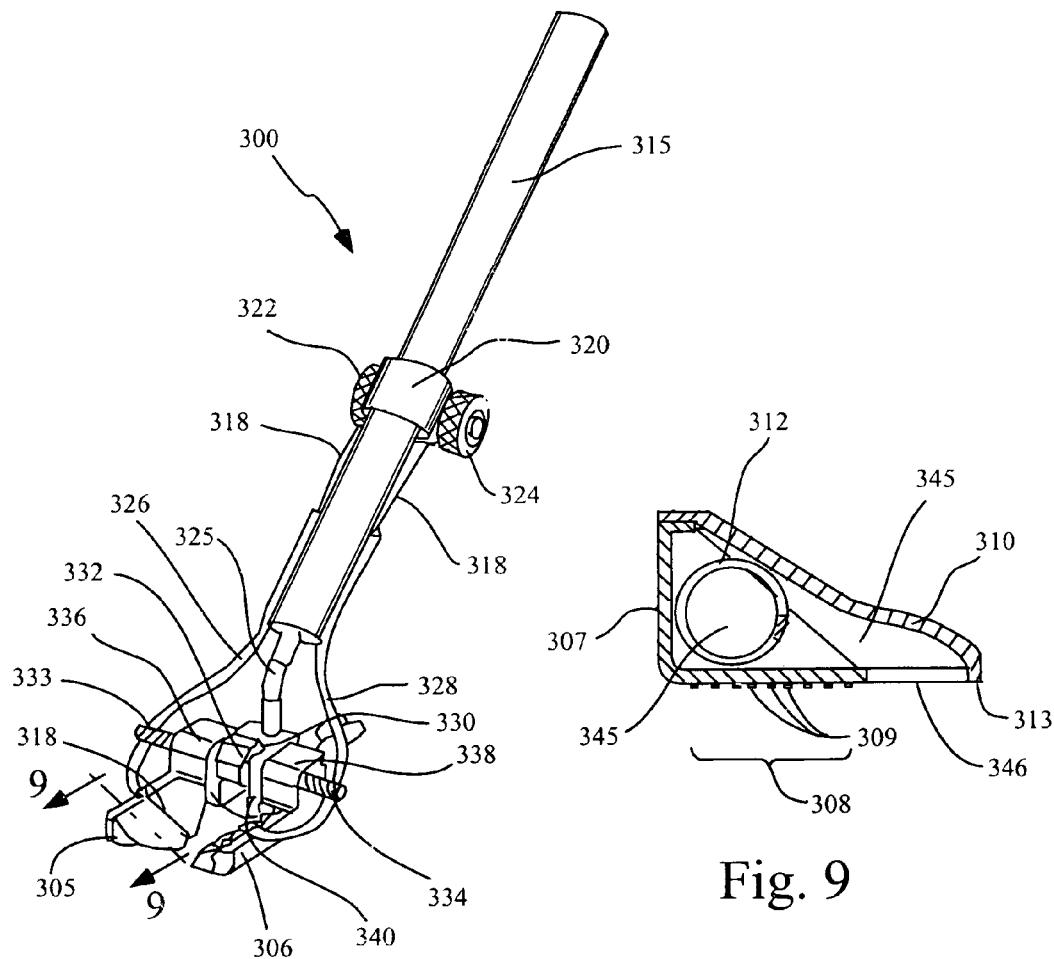
Fig. 7
Fig. 9
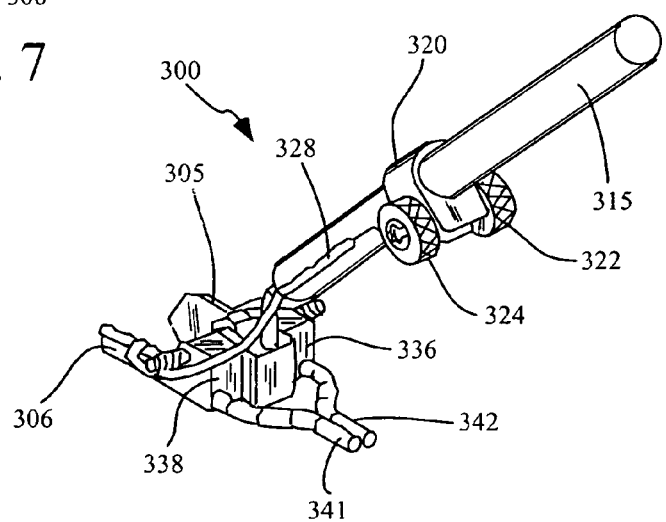
Fig. 8

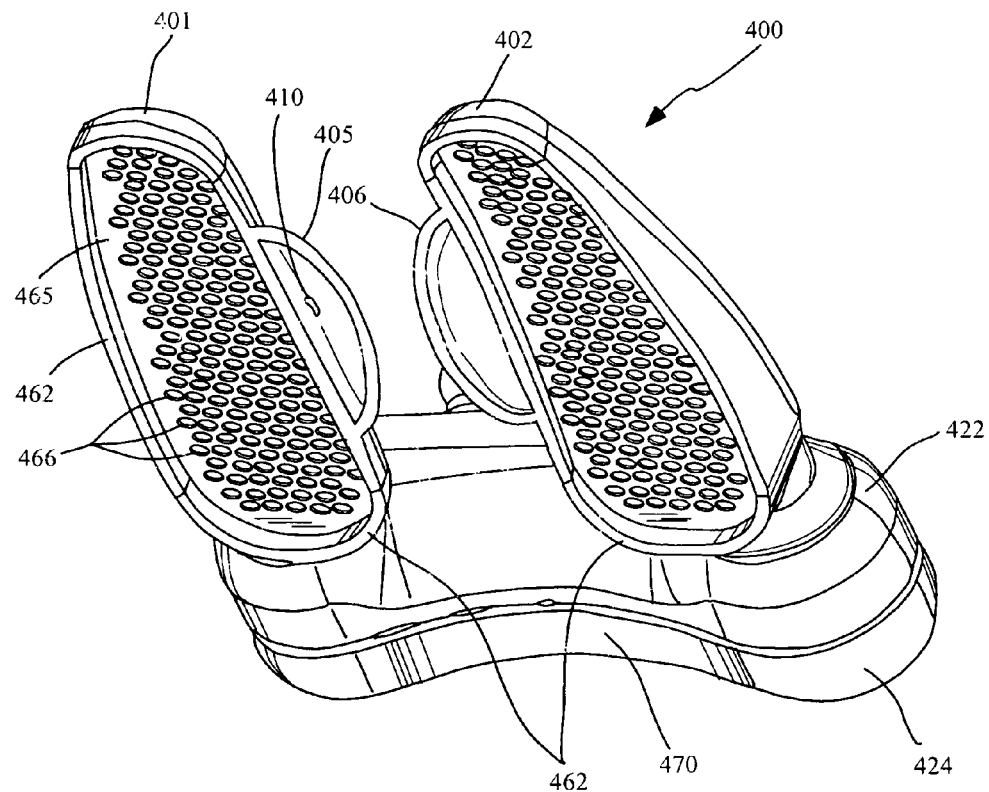
Fig. 12
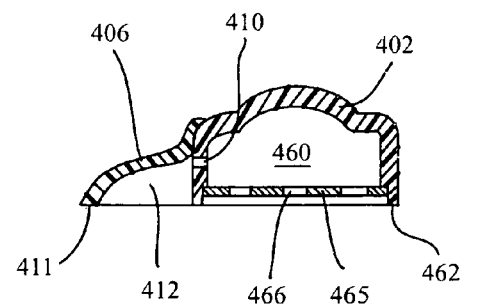 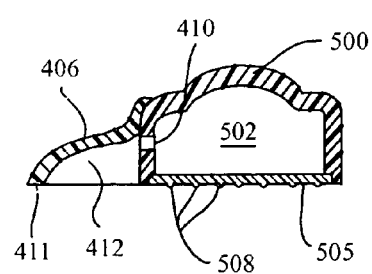
Fig. 13             Fig. 14

TISSUE STABILIZER HAVING AN ARTICULATING LIFT ELEMENT

This application is a continuation of application Ser. No. 09/398,535, filed Sep. 16, 1999, now U.S. Pat. No. 6,406,424, which is incorporated herein by reference in its entirety and to which application we claim priority under 35 USC § 120.

FIELD OF THE INVENTION

The present invention relates generally to surgical instruments, and more particularly to devices and methods for stabilizing and manipulating tissue during surgery. The tissue stabilizers described herein are particularly useful for stabilizing the beating heart during coronary artery bypass graft surgery. The field of the invention is cardiac tissue stabilizers having specially designed moveable portions.

BACKGROUND OF THE INVENTION

Certain surgical procedures require the surgeon to perform delicate operations on tissues within the body that are moving or otherwise unstable. For example, a large and growing number of surgeons are routinely performing successful coronary artery bypass graft surgery on the beating heart. In a typical coronary artery bypass graft (CABG) procedure, a blocked or restricted section of coronary artery, which normally supplies blood to a portion of the heart, is bypassed using a source vessel or a graft vessel to re-establish blood flow to the artery downstream of the blockage. This procedure requires the surgeon to create a fluid connection, or anastomosis, between the source or graft vessel and arteriotomy or incision in the coronary artery. Forming an anastomosis between two vessels in this manner is a particularly delicate procedure requiring the precise placement of tiny sutures in the tissue surrounding the arteriotomy in the coronary artery and in the source or graft vessel so that the two may be sutured together.

To ensure that the sutures may be placed with the required accuracy and precision to yield an anastomosis having long term patency, a number of devices have been developed to stabilize a portion of the heart in the vicinity of the target coronary artery. The vast majority of devices suitable for successfully stabilizing the beating heart use either compression or vacuum, or both, to engage and immobilize a portion of cardiac tissue, preferably along opposite sides of the target artery. Devices configured to use a compressive force to stabilize a surgical site on the beating heart can be found, for example, in U.S. Pat. No. 5,894,843 to Benetti et al. Examples of devices configured to use negative pressure or vacuum to stabilize or to assist in stabilizing cardiac tissue are described, for example, in U.S. Pat. Nos. 5,727,569 to Benetti et al. and 5,836,311 to Borst et al.

Although some stabilization devices reduce or eliminate the motion of the heart at the surgical site or target artery, visualization or presentation of the target artery, and more specifically the arteriotomy to which a vessel will be anastomosed, could be improved in certain surgeries. While a properly stabilized vessel will usually exhibit acceptable visualization, some operations and tissue geometries can distort the tissue surrounding the coronary artery or the coronary artery itself in a manner which complicates the completion of the anastomosis. For instance, excessive pushing on the cardiac tissue along each side of the coronary artery may tend to flatten the target artery top to bottom while pulling may tend to compress the target artery side to side as tissue is pulled higher than the target artery. In other instances, the target coronary artery is not conveniently located along the surface of the myocardium, but instead is partly or completely covered by fat or other tissue. In such cases, the stabilization forces alone can do little to optimize the visualization and presentation of the target artery.

The presentation of the target vessel and the arteriotomy is a significant factor in eliminating anastomotic errors which may cause vessel damage or a less than optimal anastomosis which may lead to failure of the anastomosis. When the arteriotomy is not optimally presented, there is a higher likelihood of incurring a surgical error in the formation of the anastomosis. To suture an anastomosis the surgeon generally works his needle from the inside vessel wall to the outside of the vessel wall. If the vessel is flattened, for example, it becomes more likely for the surgeon to accidentally catch the back wall of the vessel with the curved suture needle as the suture is placed in the tissue surrounding the arteriotomy. When the vessel is compressed side to side, it becomes more difficult to catch only the desired side of the arteriotomy without also catching the other side.

When the edges of the arteriotomy are not presented as desired, the surgeon may be required to manually manipulate the target artery using forceps or the like. The surgeon must be careful to only manipulate the vessel at the outside edges of the incision as manipulation to the interior of the vessel wall may cause damage to the soft intimal layer of the vessel leading to scarring and often late restenosis. Most often, the surgeon will try to only manipulate the tunica adventitia or outer coat of the vessel using forceps or other suitable instrument to present the arteriotomy in a manner which allows an accurate placement of each suture in the vessel from the inside out.

Even in the best of circumstances this manual manipulation of the vessel to facilitate each suture placement is tedious, time consuming, and increases the likelihood of vessel damage. This problem will become even more magnified as surgeons move to manual, computer-assisted, and robotic endoscopic procedures in which the surgeons will be attempting to complete anastomotic procedures in remote and difficult places. Delicate manipulation of the vessel walls while suturing becomes increasingly difficult as the surgeon becomes further removed from the surgical site by longer instruments, the size of the surgical site decreases leaving inadequate space to accommodate multiple instruments and the access incisions become smaller thus limiting instrument maneuverability.

In view of the foregoing, it would be desirable to have methods and devices which provide stabilization of the surgical site and target coronary artery and also provide favorable presentation of the edges of the arteriotomy so that manual manipulation of the vessel itself is reduced or eliminated. It would further be desirable to have stabilization and presentation devices which are adaptable to anatomical variations to aid in exposure of intramyocardial vessels and provide optimal vessel presentation over a wide range of operating conditions.

SUMMARY OF THE INVENTION

The present invention will be described for use during CABG surgery, but the invention is not limited thereto, and is contemplated to be useful for other surgical procedures as well. The present invention involves a tissue stabilizer having one or more stabilizer feet which are adapted to engage the heart tissue adjacent a target artery desired to be stabilized. In preferred embodiments of the present invention, the tissue stabilizer feet typically have a first foot portion which provides stabilization and a moveable portion which primarily facilitates the manipulation of the target coronary artery or local tissue surrounding the target coronary artery.

One aspect of the present invention involves a tissue stabilizer having at least one stabilizer foot having a first portion and a second portion coupled to the first portion. The first portion is preferably substantially rigid having a tissue engaging surface adapted to engage a first area on the surface of the tissue to be stabilized. The second portion may have a vacuum chamber with at least one opening adapted to engage a second area on the surface of the tissue. Preferably, the second portion is moveable relative to the first portion whereby movement of the second portion relative to the first portion manipulates the second area of tissue relative to the first area of tissue. In a preferred embodiment, the second portion, or at least a portion of the second portion, flexes, pivots, or otherwise moves upwardly relative to the first portion.

By way of example only, the tissue engaging surface may comprise a textured surface adapted to frictionally engage the first area on the surface of the tissue or may include a vacuum chamber and at least one opening in fluid communication with the vacuum chamber. When the tissue engaging surface involves a vacuum chamber, a raised seal may be disposed completely around the perimeter of the tissue engaging surface. Preferably, the raised seal is compressible so that it may conform somewhat to the surface of the tissue, but may be relatively rigid to more aggressively contact the tissue surface to form a seal.

The device may include a tension member having a distal end connected to the second foot portion. The tension member may be pulled or otherwise operated to cause the desired movement of the second portion. The tension member may be a thread material, a flexible wire, a cable, a braid, or other linkage by which the second portion can be manipulated.

The proximal end of the tension member may be connected to a tensioning mechanism. In one variation, the tensioning mechanism may include a channel adapted to receive the tension member and a locking member positioned at an angle relative to the channel and having a free end biased against the interior of said channel to trap and 5 secure a portion of the tension member between the channel and the free end. In another variation, the tensioning mechanism may comprise a pivoting member having a pivot axis. The proximal end of the tension member may be attached Co the pivoting member at a predetermined distance from the pivot axis. The tension member may also involve a spool having an outer surface about which the proximal end of the tension member may be operably connected.

In preferred embodiment, the second portion is made of a flexible material. Suitable material for the second portion may include silicone, urethane rubber, nitrile rubber, hytrel, kraton, or other medical grade flexible materials. Most preferably, the second portion comprises an elastomer.

In one preferred embodiment, the tissue stabilizer has a first stabilizer foot and a second stabilizer foot substantially parallel to the first stabilizer foot, each of the first and second stabilizer feet having a first portion and a second portion coupled to the first portion. The first portion is preferably substantially rigid and has a tissue engaging surface adapted to engage a first area on the surface of the tissue. The second portion preferably has a vacuum chamber with at least one opening adapted to engage a second area on the surface of the tissue and is moveable relative to the first portion whereby movement of the second portion relative to the first portion manipulates the second area of tissue relative to the first area of tissue. Preferably, the second portion is adapted to lift or roll up the second area of tissue relative to the first area of tissue stabilized by the first foot portions of the stabilizer feet.

Another aspect of the present invention involves a device for stabilizing tissue within a patient's body comprising at least one stabilizer foot having a first foot portion adapted to engage a first portion of tissue and a second foot portion having a vacuum space having at least one opening adapted to engage a second portion of tissue immediately adjacent the first portion of tissue, the second foot portion being flexibly coupled to the first foot portion. The tissue stabilizer may further include a tension member having its distal end operably attached to the second foot portion whereby pulling on the proximal end of the tension member causes the second foot portion to move relative to the first foot portion.

To engage the first portion of tissue, the first foot portion preferably has a vacuum chamber having at least one opening adapted to engage the first portion of tissue with negative pressure or a textured surface adapted to frictionally engage the portion of tissue. The textured surface may include a large number of small protrusions which are preferably formed by chemical machining or etching or other suitable process. To engage the second portion of tissue, the second foot portion preferably defines a vacuum space having a perimeter edge adapted to seal against the second portion tissue. Preferably, the second foot portion comprises an elastomeric material.

Another aspect of the present invention involves a device for stabilizing tissue within a patient's body for performing a surgical procedure on the tissue comprising a base member having an interior chamber and a substantially cylindrical bore and a stabilizer foot having a mating fitting positioned within said bore and being rotatable within said bore. The bore preferably has a first end in fluid communication with the interior chamber and a second end open to the exterior of the base member. The fitting is preferably substantially cylindrical having a longitudinal axis about which the fitting rotates within the bore. The stabilizer foot may have a first foot portion adapted to engage a first portion of tissue and a second foot portion adapted to engage a second portion of tissue adjacent the first portion of tissue, the second foot portion being flexibly coupled to the first foot portion.

The second portion is preferably made of an elastomer and defines a vacuum space or chamber having at least one opening in fluid communication with the second portion of tissue. Preferably, the vacuum space has a perimeter edge adapted to seal against the second portion of tissue.

Another aspect of the present invention involves a device for stabilizing tissue within a patient's body for performing a surgical procedure on the tissue comprising a first stabilizer foot having a first tissue engaging surface, a second stabilizer foot having a second tissue engaging surface, and base member having a shaft mounted for rotation relative to the base member. The shaft preferably has at least one threaded portion. The first and second tissue engaging surfaces may extend generally perpendicular to the longitudinal axis of the shaft. At least one of the stabilizer feet may be operably associated with the threaded portion of the shaft such that rotation of the shaft causes one of the stabilizer feet to move relative to the other.

In a preferred embodiment, the shaft has a first threaded portion and a second threaded portion and the first stabilizer foot is adapted to receive and traverse along the first threaded portion and the second stabilizer foot is adapted to receive and traverse along the second threaded portion. Preferably, the second threaded portion has threads which are opposite-handed to that of the threads of the first portion. With that configuration, rotation of the shaft in a first direction moves the stabilizer feet closer together while rotation in the opposite direction moves the feet further apart.

One or both of the stabilizer feet may further include a flexible member moveably coupled thereto, the flexible member having a vacuum chamber having at least one opening for engaging a portion of tissue with negative pressure. In a preferred embodiment, the flexible member comprises an elastomer.

Another aspect of the present invention involves a method of stabilizing a coronary artery on a beating heart for performing a surgical procedure on the coronary artery. The method preferably involves the steps of providing a tissue stabilizer having at least one stabilizer foot having a first portion adapted to engage a first area on the surface of the heart adjacent the coronary artery a second portion adapted to engage a second area on the surface of the heart, engaging the first area with the first portion to substantially stabilize at least a portion of the heart, engaging the second area with the second portion, and moving the second portion relative to the first portion whereby the second area of the heart is moved relative to the first area of the heart. Preferably, the second area includes at least a portion of the coronary artery.

The method may also include the step of forming an incision or arteriotomy having a first side and a second side in the coronary artery after engaging the first area with the first portion. The second area preferably includes a portion of the coronary artery adjacent to the first side of the arteriotomy whereby the step of moving the second portion relative to the first portion moves the first side of the arteriotomy relative to the second side of the arteriotomy. Once the desired side of the arteriotomy has been positioned or oriented as desired, one or more sutures may be placed through the arteriotomy or the tissue immediately adjacent the incision.

In a preferred embodiment, the tissue stabilizer has first and second stabilizer feet, each having a first portion and a second portion coupled to said first portion and moveable relative to said first portion. The method preferably includes the step of adjusting one or both of the stabilizer feet relative to each other to ensure a good fit against the surface of the heart. The first portion of each stabilizer foot may then be engaged with the surface of the heart on opposite sides of the coronary artery. An arteriotomy having a first side and a second side may be created in the coronary artery. In the preferred method, the first side is positioned relative to the second side by engaging one or both of the second portions of the stabilizer feet with the heart and moving one or both relative to the first portions. The method may also include the step of manipulating the first and second stabilizer feet relative to one another to improve presentation of the arteriotomy.

These and other features of the present invention will become more fully apparent from the following description and appended claims.

BRIEF DESCRIPTION OF THE DRAWINGS

FIGS. 7 and 8 are front and rear perspective views of a tissue stabilizer according to the principles of the present invention.

FIG. 9 is a cross-sectional view taken along line 9-9 as shown in FIG. 7.

FIG. 12 is a bottom perspective view of the tissue stabilizer of FIG. 10.

FIG. 13 is a cross-sectional view of the stabilizer foot taken along line 13-13 as shown in FIG. 10.

FIG. 14 is a cross-sectional view illustrating a vacation of the stabilizer foot of FIG. 10.

DETAILED DESCRIPTION

Figure 1:
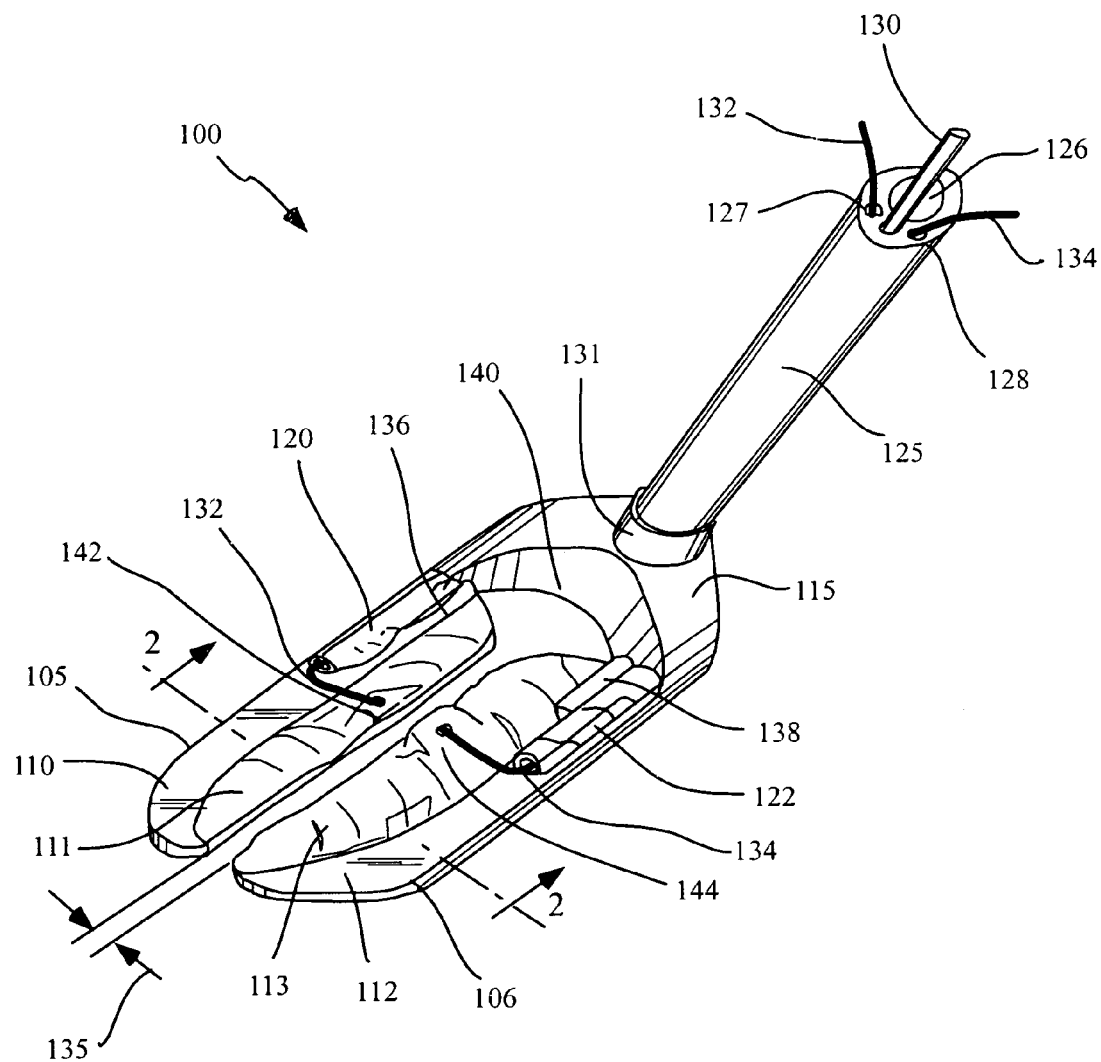
FIG. 1 is a perspective view illustrating a tissue stabilizer constructed according to the principles of the present invention.

The present invention involves devices and methods for stabilizing tissue during a surgical operation. The devices described herein may be used in a wide variety of surgical applications that require a tissue structure to be stabilized or immobilized to provide a substantially stable and motionless surgical field on which a surgical procedure can be performed. By way of example only, the preferred embodiments described in detail below are directed to the stabilization of a portion of the heart to facilitate a surgical procedure on or within the heart, such as a coronary artery bypass graft (CABG) procedure.

Although the devices and methods of the present invention may be applied to conventional stopped-heart and beating heart procedures, they are preferably used to stabilize the beating heart during a CABG operation which has been specially developed to facilitate completion of an anastomosis, typically between a target coronary artery and a bypass graft or source artery, without requiring cardiac arrest and without cardiopulmonary bypass.

A typical beating heart CABG procedure involves accessing the beating heart by way of a sternotomy, mini-sternotomy, thoracotomy, mini thoracotomy, or other suitable access incision, positioning a tissue stabilizer on, around, or adjacent a coronary artery to stabilize the coronary artery, creating an arteriotomy in the coronary artery, and forming an anastomosis between the bypass graft or source artery and the arteriotomy. Typically, the tissue stabilizer has a heart engaging member at one end for engaging the surface of the beating heart and is connected at the other end to a stationary object such as a sternal retractor, rib retractor, or other such stationary structure. Exemplar devices and methods for accessing the beating heart and mounting a stabilizer device are disclosed in co-pending U.S. patent application Ser. No. 09/305,810 titled "A SURGICAL RETRACTOR APPARATUS FOR OPERATING ON THE HEART THROUGH AN INCISION", the entirety of which is herein incorporated by reference.

The tissue stabilizers of the present invention generally have one or more stabilizer feet which are adapted to contact the heart tissue adjacent the target artery desired to be stabilized. In preferred embodiments of the present invention, the tissue stabilizer feet typically have a relatively rigid portion which provides the bulk of the tissue stabilization and a moveable or flexible portion which facilitates the fine manipulation of the target coronary artery or the local tissue surrounding the target coronary artery.

The rigid portion is sufficiently rigid to facilitate effective immobilization of at least a portion of the cardiac tissue surrounding a target artery to be stabilized, generally using a compressive force, negative pressure, or both. Preferably, the moveable or flexible portion is adapted to engage a portion of a target artery in the vicinity of an arteriotomy and may be activated to manipulate the engaged portion to obtain an optimum presentation of the edges of an arteriotomy for the purpose of completing a successful anastomosis. Generally, the moveable or flexible portion operates to lift, and more preferably to lift and retract the engaged portion of tissue. In a preferred configuration, the stabilizer foot has a moveable or flexible portion which can be articulated relative to the relatively rigid portion.

Figure 2:
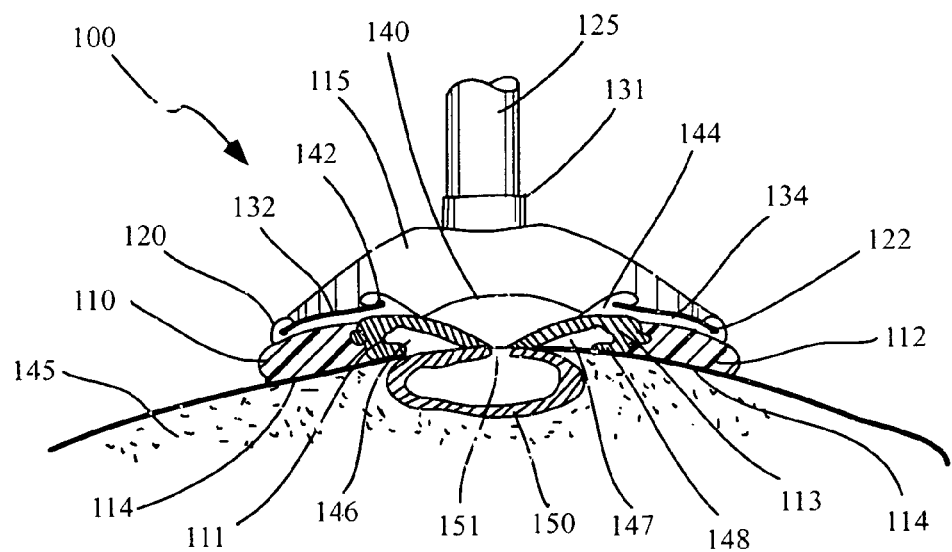
FIG. 2 is a cross-sectional view taken generally along line 2-2 of FIG. 1 illustrating the unactuated tissue stabilizer over a target vessel.
Figure 3:
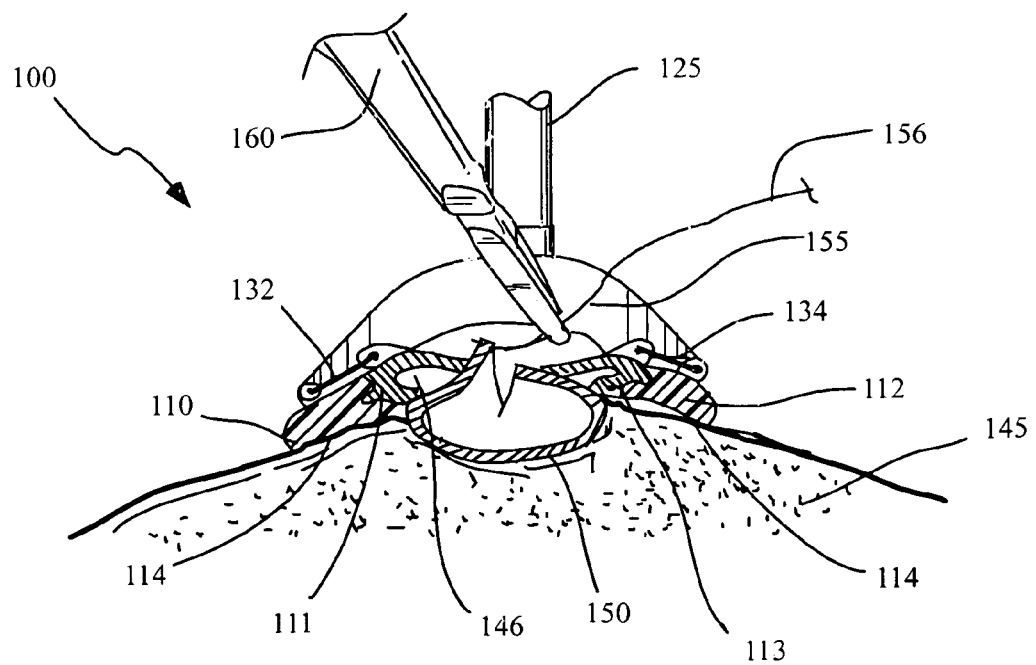
FIG. 3 is a cross-sectional view taken generally along line 2-2 of FIG. 1 illustrating the tissue stabilizer over a target vessel, but the position is altered to show the stabilizer in an actuated position.

Referring to the figures wherein like numerals indicate like elements, a preferred tissue stabilizer is illustrated in FIGS. 1-3. Tissue stabilizer 100 preferably has first and second stabilizer feet 105 and 106 which are typically oriented and spaced apart an appropriated distance to engage the surface of the heart on opposite sides of a target coronary artery in an adult human patient. Tissue stabilizer 100 is typically positioned such that the coronary artery runs lengthwise in the space between stabilizer feet 105 and 106.

For beating heart procedures where it is often, although not universally, undesirable to occlude the target vessel, tissue stabilizer 100 preferably has a construction that does not occlude of otherwise compress the target coronary artery as stabilizer feet 105 and 106 are placed on opposite sides of the vessel to be stabilized. When stabilizer feet 105 and 106 are connected to a common support member or base, the base may include a recessed or raised portion to ensure that the vessel does not become occluded by stabilizer feet 105 and 106. For example, base 115, which generally spans over a portion of the target coronary artery to structurally connect stabibzer feet 105 and 106, preferably has a raised portion or bridge 140 under which the coronary vessel may pass without being significantly compressed or occluded when stabilizer feet 105 and 106 are engaged to stabilize the heart in the vicinity of the target vessel.

Stabilizer feet 105 and 106 are connected to base 115 which typically has mounting or connecting features for operably attaching a suitable stabilizer shaft or other such structure which in turn may be mounted to a stable platform such as a retractor. The construction of the shaft and attachment to base 115 may be any suitable configuration which allows the desired maneuverability of the tissue stabilizer relative to the shaft. Tissue stabilizer 100 preferably has shaft 125 connected to base 115 at distal connection 131.

Shaft 125 may have a number of functions and features. Preferably, shaft 125 includes vacuum lumen 126 for supplying a negative pressure to a chamber or manifold (not shown) within base 115, and ultimately to stabilizer feet 105 and 106. In one embodiment, shaft 125 is made of a flexible material having a support rod 130. Support rod 130 is preferably of sufficient rigidity to impart the required stabilization forces to stabilizer feet 105 and 106. In one embodiment, at least a portion of support rod 130 may be malleable to allow the device to be oriented and positioned as desired.

In a preferred embodiment, stabilizer feet 105 and 106 have fixed or substantially rigid portions 110 and 112 and moveable portions 111 and 113, respectively. Rigid portion 110 and 112 extend from base 115 and are adapted to engage the surface of heart 145 adjacent the target artery (See FIGS. 2-3). In this embodiment, rigid portions 110 and 112 have tissue engaging or contacting surfaces 114 which are preferably roughened or textured to ensure that the device does not slip relative to the surface of the heart when tissue contacting surfaces 114 are pressed against the heart. Tissue contacting surfaces 114 are preferably textured using a chemical machining or like process.

Moveable portions 111 and 113 are preferably positioned inside of rigid portions 110 and 112. The interior edges of moveable portions 111 and 113 are separated by a small distance 135 which may range from essentially zero to a distance which is slightly larger than the target vessel to be stabilized. Moveable portions 111 and 113 are preferably positioned to engage the tissue immediately surrounding the target vessel, and if desired, a portion of the target vessel wall itself so that the arteriotomy may be presented for suturing by articulating moveable portions 111 and 113. Referring to FIG. 1, distance 135 is preferably less than about 0.2 inches, more preferably less than about 0.125 inches.

Preferably, moveable portions 111 and 113 maybe articulated relative to rigid portions 110 and 112. As will be discussed in detail below with reference to FIG. 6, moveable portions 111 and 113 may be a rigid member which articulates relative to the rigid foot portions, for example, by way of a pivot, hinge, linkage, or other mechanism. However, simple mechanisms and single axis pivots do not generally provide a motion of the moveable portion which matches the natural shape and curvature of the edges of the fixed length incision of a standard arteriotomy as it is urged open for suturing. The edges of an incision creating an arteriotomy somewhat resembles a shape like two open eyelids. As this shape is difficult to produce with single axis rotation, moveable portions 111 and 113 are preferably thin elastically deformable members. In preferred embodiment, moveable portions 111 and 113 may be made from a medical grade elastomer or other flexible material such as, for example, silicone, urethane rubber, nitrile rubber, hytrel, kraton, or other medical grade material.

In a preferred embodiment, moveable portions 111 and 113 are elastic members having a tension member attached thereto, preferably at the center of moveable portions 111 and 113. By pulling back on the elastic members using central tension member, the elastic material creates a compound curve which mimics the natural shape of the arteriotomy as it is pulled open. Thus, when moveable portions 111 and 113 are provided with a means for engaging the exterior of target artery 150, it is able to pull open arteriotomy 151 with a compound shape that does not harm or stress the target artery or the arteriotomy. Preferably, the compound deflected shape of moveable portions 111 and 113 tend to lift, and more preferably lift and retract, the edges of the arteriotomy.

The means for engaging the exterior of the target artery, or other surrounding tissue, may include suitably positioned vacuum chambers, suction ports, sutures or the like fixing the moveable portions 111 and 113 to the tissue structure to be moved, adhesive tapes or substrates, or any other suitable instrumentality for engaging the desired tissue structure so that it may be lifted or otherwise manipulated as moveable portions 111 and 113 are articulated. In a preferred embodiment, moveable portions 111 and 113 have vacuum chambers 146 and 147, respectively, positioned and adapted to engage the exterior of the target artery or other surrounding tissue. In a preferred embodiment, vacuum is supplied to vacuum chambers 146 and 147 through vacuum tubes 136 and 138 which are fluidly connected to base 115 which is in fluid communication with vacuum lumen 126 of shaft 125.

Moveable portions 111 and 113 may have base extension 148 adapted to contact the heart forming part of the perimeter seal around vacuum chambers 146 and 147. The length of base extension 148, at least in part, determines the width of the vacuum opening which will engage tissue. A base extension having a longer length tends to limit the tissue engaged by the negative pressure within vacuum chambers 146 and 147 to potentially only the exterior surface of target artery 150. If it is desired to also capture a greater amount of the tissue surrounding target artery 150, then base extension 148 can be shortened or eliminated. In an optional embodiment, base extension 148 may extend completely across vacuum chambers 146 and 147 to form an integral bottom of a completely enclosed sealed chamber. The integral bottom may have one or more holes or openings appropriately placed to engage the desired portion of the target artery or surrounding tissue with the negative pressure supplied within the chamber.

Articulation of moveable portions 111 and 113 is preferably accomplished by pulling using a tension member or other such linkage. Preferably, the tension member is in the form of a flexible wire, cable, braid, or suture thread, such as pull wires 132 and 134. Pull wires 132 and 134 may be routed proximally on the device for easy access. Preferably, pull wires 132 and 134 are attached to moveable members 111 and 113 at attachment bosses 142 and 144 and routed through guide tubes 120 and 122 and through wire lumen 127 and 128 provided in support shaft 125. The proximal ends of pull wires 132 and 134 may be accessed by the surgeon directly using a suitable instrument or may be attached to any suitable automated tensioning device, an example of which is discussed below with reference to FIG. 4.

To perform the desired suturing around the edges of an arteriotomy, tissue stabilizer 100 is brought into contact with the surface of heart 145, with stabilizer feet 105 and 106 positioned on opposite sides of target vessel 150. A stabilizing force is delivered to stabilizer feet 105 and 106 by way of shaft 125 and shaft 125 is typically secured in place to a rigid support such as a sternal or rib retractor. With a localized portion of the beating heart stabilized under rigid portions 110 and 112, arteriotomy 151 is created in target vessel 150 as shown in FIG. 2. A negative pressure is introduced to vacuum lumen 126 which is communicated to vacuum chambers 146 and 147 within moveable portions 111 and 113 thus causing moveable portions 111 and 113 to become engaged with target artery 150.

Next one of the moveable portions, 111 for example, is articulated as shown in FIG. 3 optimally presenting one edge of the arteriotomy to allow needle 155 having suture thread 156 to be accurately placed in the edge of the arteriotomy, typically using a long forceps 160 or like instrument (or end effector if the procedure is being performed robotically). After all the suturing has been completed along the edge of the arteriotomy being presented by moveable portion 111, pull wire 132 is released. The opposite side of the arteriotomy may then be presented by articulating moveable portion 113 using pull wire 134. If desired, both moveable portions 111 and 113 maybe articulated at the same time to lift up on both sides of the arteriotomy.

Figure 4:
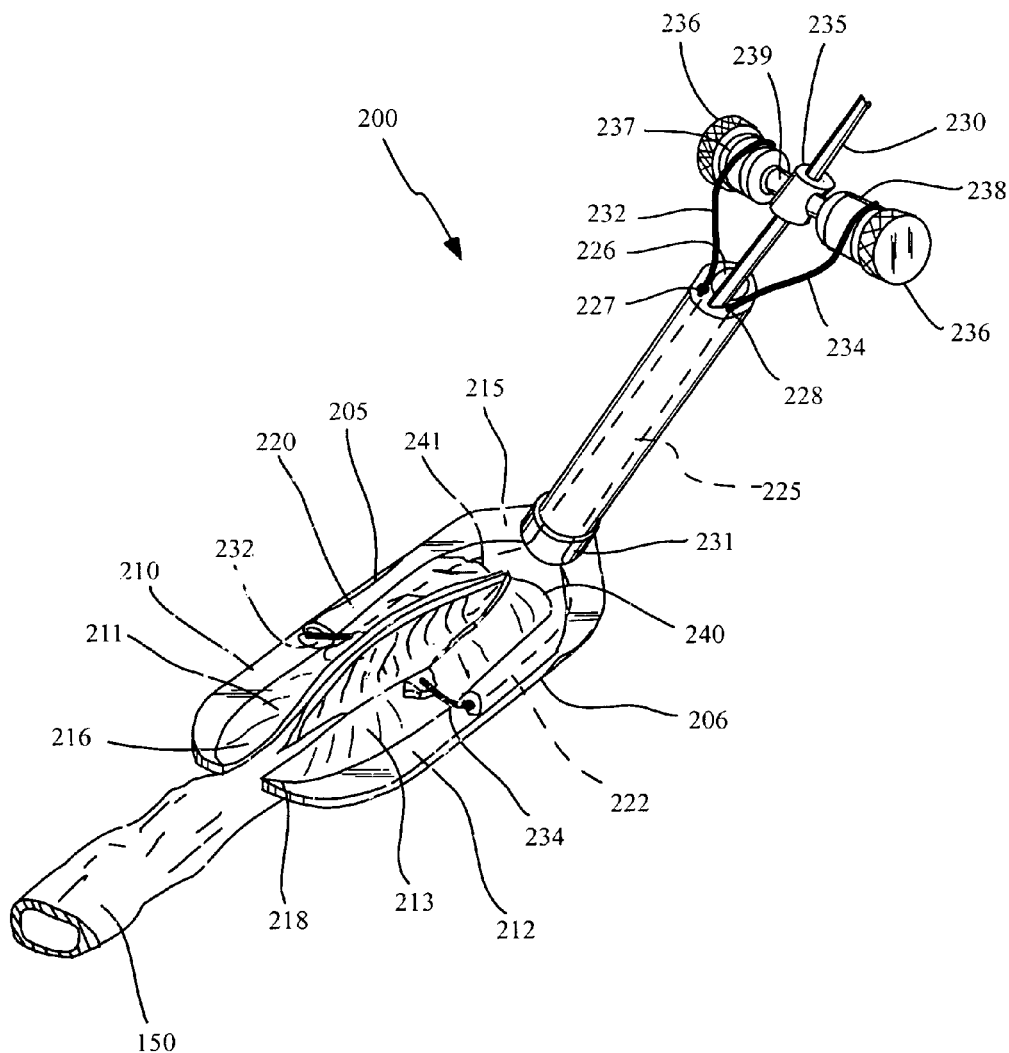
FIG. 4 is a perspective view illustrating another tissue stabilizer according to the principles of the present invention.

A tissue stabilizer having a tension member actuator is illustrated in FIG. 4. Tissue stabilizer 200 again has a first and second stabilizer feet 205 and 206 attached to base 215 to which shaft 225 is connected at distal connection 231. Stabilizer feet 205 and 206 have fixed or rigid portions 210 and 212 and flexible or moveable portions 211 and 213, respectively. Moveable portions 211 and 213 preferably have vacuum chambers adapted to engage the desired tissue structure as described above.

In the embodiment illustrated in FIG. 4, the vacuum chambers of moveable portions 211 and 213 are fluidly connected directly to base member 215 at base connections 240 and 241. In addition, rigid portions 210 and 212 are relieved somewhat so that the material of moveable portions 211 and 213 can be extended to form flexible tips 216 and 218. Flexible tips 216 and 218 further protect against any unwanted compression of target artery 150 at the tip region of the device as the stabilization forces are supplied through rigid portions 210 and 212 to the surface of the heart.

Moveable portions 211 and 213 may be actuated by any suitable linkage, lever, articulating mechanism or tension member. Preferably moveable portions 211 and 213 have tension members 232 and 234 attached centrally thereto. Tension members 232 and 234 are preferably made of suture thread, wire, cable, braid, ribbon or the like. Tension members 232 and 234 are routed through guide tubes 220 and 222 and into guide lumen 227 and 228 associated with shaft 225. Tension members 232 and 234 may be connected proximally to any suitable actuator mechanism which allows the user to conveniently apply an appropriate force to tension members 232 and 234 to cause moveable portions 211 and 213 to retract as desired to effectuate an optimum presentation of target vessel In a preferred embodiment, the actuator mechanism comprises one or more rotating elements or spools for winding up tension members 232 and 234, thereby causing the desired articulation of moveable members 211 and 213. Preferably, collar 235 is attached to a structural member or rod 230 which extends through at least a portion of shaft 225. Axle or pin 239 extends from collar 235, preferably from opposite sides. Spools 237 and 238 have a mating bore for receiving and pivotally rotating about pin 239. The proximal ends of tension members 237 and 238 are connected to or wrapped around spools 237 and 238 such that rotation of the spools causes tension members 237 and 238 to wind up, thus pulling on moveable portions 211 and 213 at their distal attachments. Each spool may have a knurled knob 236 or the like to facilitate convenient actuation of the mechanism by the user.

Figure 5:
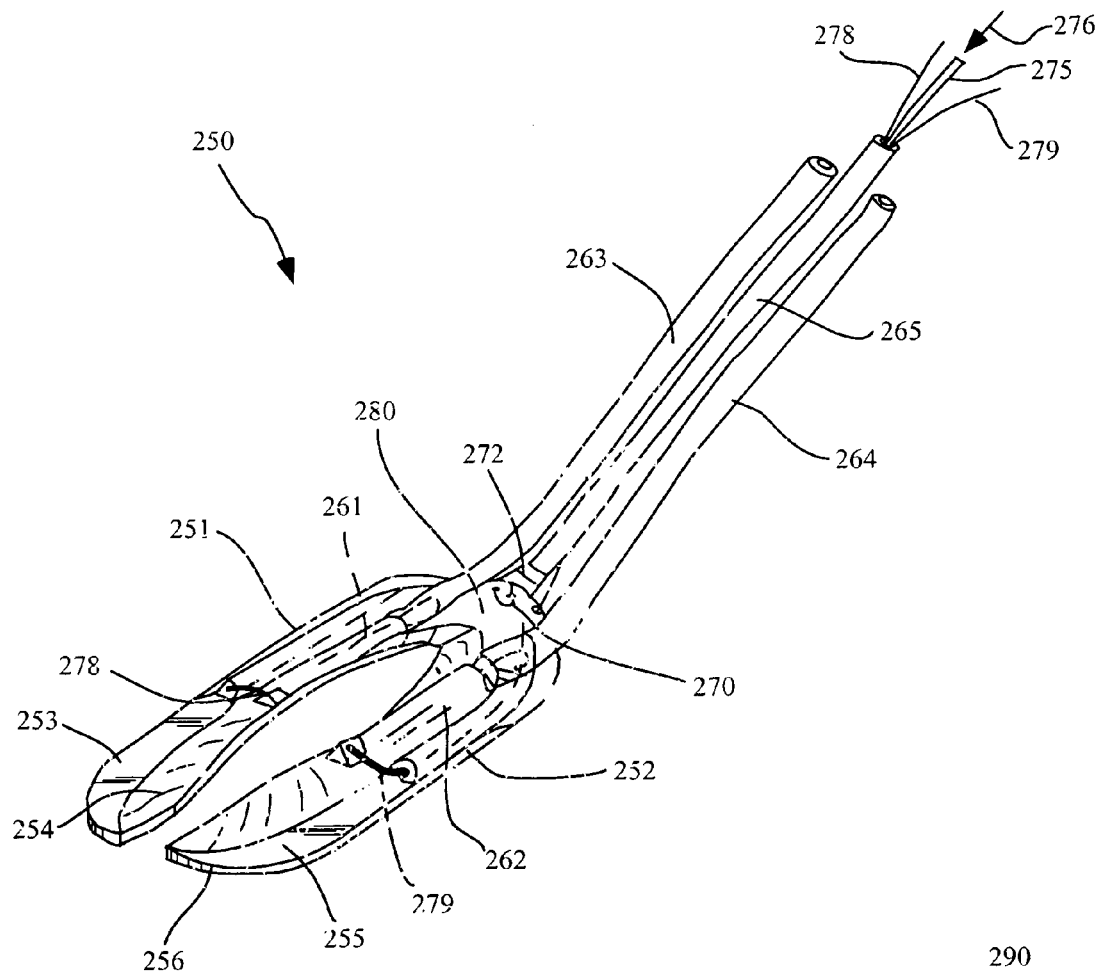
FIG. 5 is a perspective view of an alternative embodiment of the tissue stabilizer of the present invention.

Another embodiment of a tissue stabilizer constructed according to the principles of the present invention is illustrated in FIG. 5. Tissue stabilizer 250 has first and second feet 251 and 252 having rigid portions 253 and 255 and moveable portions 254 and 256 which articulate in response to pulling on tension members 278 and 279. Moveable portions 254 and 256 have vacuum connections 261 and 262 individually associated therewith. Vacuum supply lines 263 and 264 can be directly connected to vacuum connections 261 and 262 to communicate negative pressure to the vacuum chambers of moveable portions 254 and 256.

With the vacuum supply lines connected directly to moveable portions 254 and 256, base member 280 is not required to function as a manifold to communicate negative pressure from a vacuum lumen to the stabilizer feet, but need only be a substantially rigid structure to which stabilizer feet 251 and 252 are operably connected. Further, the shaft used to stabilize and transmit the required stabilizing forces to the stabilizer feet becomes unburdened from the requirement of having a vacuum lumen as described in the previous examples.

In a preferred embodiment, base 280 has a ball 270 extending upwardly therefrom to which shaft 265 having a distal housing 272 having a socket for mating with ball 270. Preferably shaft 265 is substantially rigid and may have a center rod 275 which may be forced in the direction of arrow 276 to prevent any relative movement between ball 270 and distal housing 272. This arrangement allows the orientation of the stabilizer feet to be adjusted as desired and then locked into place for the application of the stabilizing forces through shaft 265. Suitable constructions for ball 270, shaft 265, center rod 275 and mechanisms for causing enter rod 275 to lock the ball and housing in place can be found, for example, in U.S. Pat. No. 6,036,641 and EPO Serial No. 97102789.1, the entireties of which are herein incorporated by reference.

Figure 6:
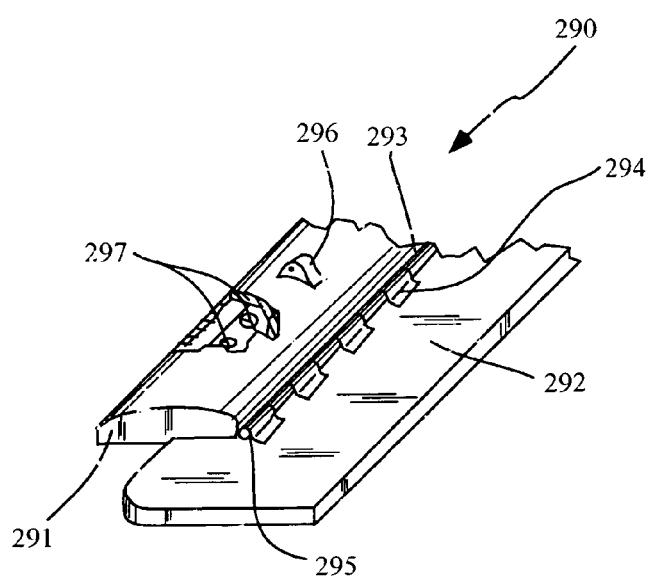
FIG. 6 is a partial perspective view of a stabilizer foot illustrating an alternative articulating member.

As mentioned above, the moveable portions of the stabilizer feet of the present invention are preferably made of a flexible material which elastically deforms to a desirable shape for presenting the edges of an arteriotomy of a target vessel. It should be noted however that other materials and configurations are intended to be within the scope of the present invention. FIG. 6, for example, illustrates a stabilizer foot variation in which the moveable portion of the stabilizer foot is connected to the rigid portion by way of a pivot or hinge. Preferably, stabilizer foot 290 has a fixed foot portion 292 and a pivotally connected articulating member 291. In a preferred embodiment, articulating member 291 and fixed foot portion 292 have an alignment of alternating cylinders 293 and 294, respectively, through which a pin or rod 295 may be inserted to create a hinge.

Preferably, fixed foot portion 292 is sufficiently rigid to provide adequate stabilization of the tissue at the surgical site. Articulating member 291 is adapted to engage the target artery or immediately surrounding tissue. Once the desired tissue 291 is engaged, articulating member 291 can be manipulated to lift the tissue to improve the surgical presentation. A tension member or other suitable link may be connected to raised boss 296 to effectuate the desired articulation.

Articulating member 291 may engage the desired tissue in any suitable manner, including tissue adhesives, negative pressure, sutures, etc. In a preferred embodiment, articulating member 291 has a sealed, hollow configuration to which a negative pressure can be communicated. One or more holes or openings 297 adapted to engage the desired tissue structure may be provided in a suitable location on the bottom of articulating member 291.

In addition to articulation of the moveable portions of the stabilizer feet, it may be desirable to have the ability to adjust the position of one or both of the stabilizer feet to account for anatomical variations and surgeon preference. In one embodiment, illustrated with reference to FIGS. 7-9, tissue stabilizer 300 is provided with stabilizer feet 305 and 306 which may be adjusted relative to one another to provide the desired spacing between stabilizer feet 305 and 306.

Preferably, stabilizer feet 305 and 306 have or are connected to threaded blocks 336 and 338, respectively. Central base housing 330 has a pair of flanges 340 between which knob 332 is housed. Knob 332 has right-hand threaded shaft 334 for cooperating with right-hand threads in block 338 and left-hand threaded shaft 333 for cooperating with left-hand threads in block 336. With this configuration rotation of knob 332 in one direction spreads stabilizer feet 305 and 306 apart while an opposite rotation brings stabilizer feet 305 and 306 closer together. Thus, the spacing between the stabilizer feet can be adjusted to properly position the vessel relative to the stabilizer feet, and in particular relative to the moveable portion. This tends to ensure that the articulating portion of the stabilizer feet engages and lifts the desired portion of the target artery and surrounding tissue.

Stabilizer feet 305 and 306 illustrate another variation of stabilizer feet having a flexible articulating portion for lifting the target artery or surrounding tissue to improve surgical presentation of the tissue structure to be sutured or otherwise operated upon. Referring specifically to FIG. 9, this stabilizer foot variation involves a stabilizer foot having relatively rigid member 307 and a moveable or flexible member 310, which together form an enclosed vacuum space or chamber 345 having an opening 346 for engaging a tissue structure when negative pressure is present in chamber 345. Flexible member 310 preferably includes a perimeter edge 313 for creating a seal against the tissue structure. Coil spring 312, or other suitable mesh or screen member, is preferably positioned within chamber 345 to prevent excessive collapse of flexible member 310 into rigid member 307.

Rigid member 307 preferably has a tissue contacting region 308 having a roughened surface which may include a large number of small projections 309 to provide the necessary traction against the surface of the beating heart. The roughed surface may be formed by coining, laser cutting, milling, chemical machining or like process. The surgical site is stabilized by applying a suitable stabilizing force to stabilizer feet 305 and 306, which engage the heart at tissue contacting regions 308, by way of stabilizing shaft 315. Stabilizing shaft 315 may be connected to central base housing 330 using any connection which provides the desired maneuverability of stabilizer feet 305 and 306 relative to stabilizing shaft 315. In one embodiment, stabilizing shaft 315 is operably connected to central base housing 330 by way of a malleable link 325 which allows the orientation of the stabilizer feet to be manually oriented but is sufficiently rigid to provide the required stabilization of the surgical site. In another embodiment, stabilizing shaft 315 may be connected to central base housing 330 using a suitable ball and socket joint as set forth above with respect to FIG. 5.

Flexible member 310 is preferably articulated using tension members 318 routed through guide tubes 326 and 328 which are connected proximally to stabilizer shaft 315. Guide tubes 326 and 328 are preferably sufficiently flexible or malleable to follow stabilizer feet 305 and 306 in and out without adversely affecting the operation of tension members 318. The proximal ends of tension members 318 may be connected to any suitable device that allows for convenient tensioning to produce the desired articulation of flexible member 310. Preferably, the proximal ends of tension members 318 are connected to rotating spools 322 and 324 affixed to collar 320 on stabilizer shaft 315.

Another tissue stabilizer embodiment having adjustable stabilizer feet is illustrated in FIGS. 10-13. Tissue stabilizer 400 has first and second stabilizer feet 401 and 402 operably connected to manifold base 420. Stabilizer feet 401 and 402 preferably have features for engaging the surface of the heart to facilitate stabilization of at least a portion of the heart. In a preferred embodiment, stabilizer feet 401 and 402 are connected to manifold base 420 in a manner which allows each foot to independently rotate relative to the manifold base 420. The axes about which stabilizer feet 401 and 402 rotate may be in any orientation that provides the desired stabilizer feet orientation relative to the heart to achieve optimum engagement or tissue presentation. Preferably, the axes are offset vertically from the features which engage the surface of the heart. Suitable tissue stabilizer constructions having rotatable stabilizer feet are described in co-pending U.S. patent application Ser. No. 09/366,190, filed on Jun. 21, 1999 and titled "TISSUE STABILIZER AND METHODS OF USE", the entirety of which is herein incorporated by reference.

Figure 11:
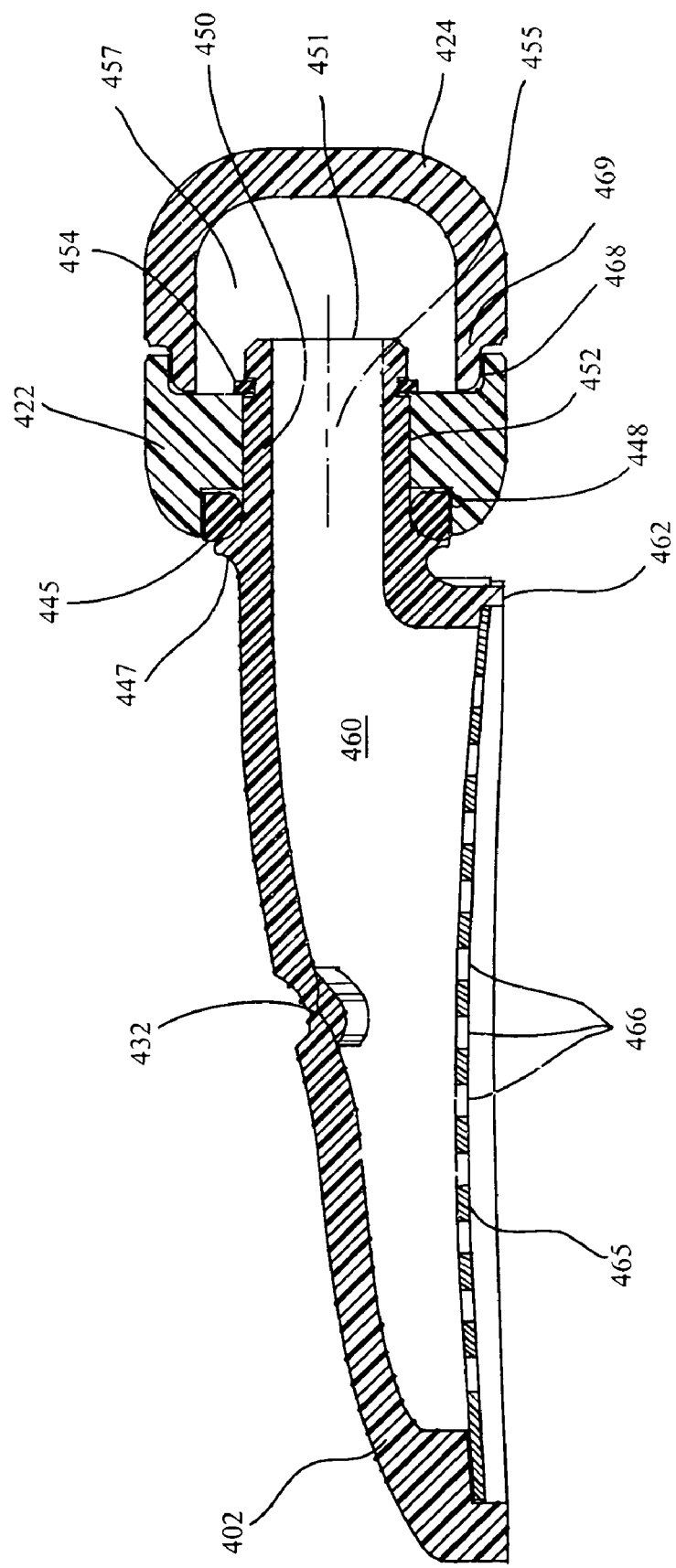
FIG. 11 is a cross-sectional view taken along line 11-11 as shown in FIG. 10.

Referring to FIG. 11, a preferred stabilizer foot connection is illustrated with respect to stabilizer foot 402. Manifold base 420 has a bore 452 extending through an exterior wall. Stabilizer foot 402 has an end portion or fitting 450 having an outside diameter adapted to mate with bore 452 to allow fitting 450, and thus stabilizer foot 402, to rotate about central axis 455 of fitting 450. When stabilizer feet 401 and 402 are rotatable in this manner, their orientation may be adjusted to account for anatomical differences to obtain the best possible engagement against the surface of the tissue to be stabilized.

Preferably, central axis 455 is offset vertically from the features on the stabilizer feet which engage the surface of the heart. This offset facilitates a measure of improved vessel presentation as stabilizer feet 401 and 402 are rotated because, in addition to changing the overall orientation of the tissue engaging features, the eccentric relation of the tissue engagement features relative to central axis 455 moves the stabilizer feet together or apart as the stabilizer feet are rotated. This action allows the tissue and included target artery between the stabilizer feet to be stretched or compressed as desired by rotating either or both of stabilizer feet 401 and 402 after they have become operably engaged with the tissue.

In a preferred embodiment, tissue stabilizer 400 is constructed to supply a negative pressure or vacuum to stabilizer feet 401 and 402 to assist in the engagement of the surface of the heart. Stabilizer feet 401 and 402 preferably have a vacuum chamber 460 to which a vacuum may be supplied through vacuum inlet 451 of fitting 455. Vacuum inlet 451 is in fluid communication with a hollow interior chamber or space 457 within manifold base 420 to which negative pressure may be supplied by way of barbed exterior fitting 426.

To allow vacuum to be communicated from manifold base 420 to the engagement features of stabilizer feet 401 and 402, the rotating connection between stabilizer feet 401 and 402 and manifold base 420 must be sealed to prevent any significant vacuum loss. This is preferably accomplished using an appropriate dynamic annular or shaft seal that seals between the stabilizer feet and manifold base 120 but yet allows for rotation of the stabilizer foot within bore 452 without incurring any vacuum loss. Preferably, O-ring 445 is positioned within an annular seal cavity 448 at the entrance of bore 452. O-ring 445 is captured and compressed within seal cavity 448 by cooperating annular seal flange 447 provided on stabilizer feet 401 and 402 as the stabilizer feet are urged into final position. Stabilizer feet 401 and 402 may be held in position by operation of an external retaining clip 454 assembled to fitting 450 just beyond its exit of bore 452.

Vacuum chamber 460 is generally a closed chamber except for one or more openings for engaging the surface of the heart. Preferably, stabilizer feet 401 and 402 have a substantially continuous perimeter sealing member 462 for engaging the surface of the heart. When perimeter sealing member 462 makes contact with the surface of the heart around substantially its entire perimeter, the portion of the heart tissue within the perimeter is subjected to the negative pressure existing within vacuum chamber 460 and is urged into engagement with stabilizer feet 401 and 402. The negative or vacuum pressure may be sufficient to displace that portion of heart tissue with the vacuum chamber created by perimeter sealing member 462 into forced contact with perforated sheet member 465 having holes or openings 466.

For ease of manufacturing and assembly, manifold base 420 is preferably made in two or more portions and fixed together to form the sealed, hollow interior space 420. In a preferred embodiment, manifold base 420 has front manifold portion 422 and rear manifold portion 424 which may be fixed together using standard mechanical fasteners, a snap fit construction, or any suitable adhesive, bonding, sealing or welding technique compatible with the material of manifold base 420. Manifold base 420 is preferably made from an injection molded plastic suitable for surgical sterilization.

To facilitate reliable bonding between front and rear manifold portions 422 and 424, rear manifold portion 424 has an inner flange 469 and front manifold portion 422 has an overlapping outer flange 468. This overlapping flange configuration provides a reliable seal between manifold portions, especially when used in conjunction with a suitable gap-filling adhesive or bonding agent.

Similar to the previously discussed embodiments, stabilizer feet 401 and 402 have flexible members 405 and 406 which may be elastically manipulated using attached tension members 430 to aid in the surgical presentation of the tissue structure on which a surgical procedure is to be performed. Flexible members 405 and 406 preferably define a vacuum space 412 for engaging the target artery or surrounding tissue. Flexible members 405 and 406 are centrally disposed relative to stabilizer feet 401 and 402 and preferably have a curved outer profile having the greatest extension near its center region. A curved configuration provides the greatest manipulation of the target artery at the center and leaving the ends of the arteriotomy somewhat less obstructed for improved access.

Vacuum space 412 is supplied negative pressure from vacuum chamber 460 through opening or aperture 410. The aperture is preferably sized to restrict the amount of vacuum flow so that vacuum chamber 460 is able to continue to hold the necessary vacuum to maintain engagement and stabilization in the event a leak develops around sealing edge 411 of flexible members 405 or 406. In a preferred embodiment, at least a portion of stabilizer feet 401 and 402 is made from a clear material to aid in visually determining if any portion of the perimeter seals have a vacuum leak by observing blood or other material being sucked into vacuum chamber 460 or vacuum space 412.

Instead of engaging the tissue using negative pressure communicated through perforated sheet 465 the tissue stabilizer may be provided with stabilizer feet having a tissue contacting surface for frictionally engaging the surface of the heart. Referring to FIG. 14, stabilizer foot 500 is constructed essentially similar to stabilizer feet 401 and 402 except that stabilizer foot 500 has a solid tissue contacting surface 505, preferably having a roughened texture which may include a number of projections 508 for increasing the lateral grip against the surface of the heart. Stabilizer foot 500 has a sealed, hollow interior 502 which accumulates negative pressure for communication to vacuum space 412 through opening or aperture 410.

As mentioned above, tension members 430 may be used to articulate moveable members 405 and 406. Tension members 430 may be routed proximally in or along a stabilizing shaft (not shown) which is preferably operably connected at ball 428 extending from manifold base 420 and may be connected to a tensioning mechanism located on the shaft. In another embodiment, tensioning members 430 may be tensioned manually using forceps or the like until the desired manipulation of moveable members 405 and 406 has been achieved and then locked into place using a suitable thread locking mechanism, spring, clip, clamp, or the like.

Figure 10:
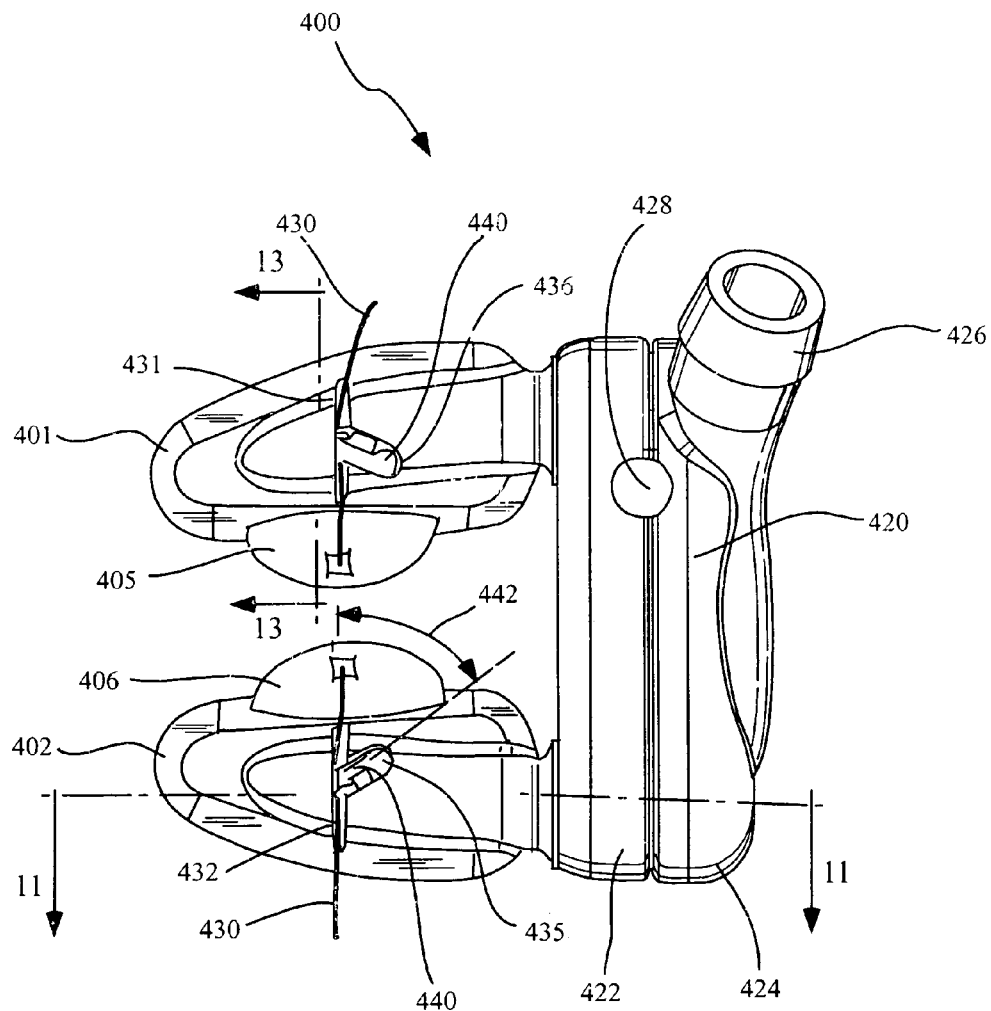
FIG. 10 is a top plan view illustrating another embodiment of the tissue stabilizer of the present invention.

In a preferred embodiment illustrated in FIG. 10, stabilizer feet 401 and 402 have suture locking devices for holding the desired tension or position of tension members 430. Preferably stabilizer feet 401 and 402 have channels 431 and 432 for receiving tension members 430 and cavities 436 and 435 for receiving suture locking members 440.

Figure 15:
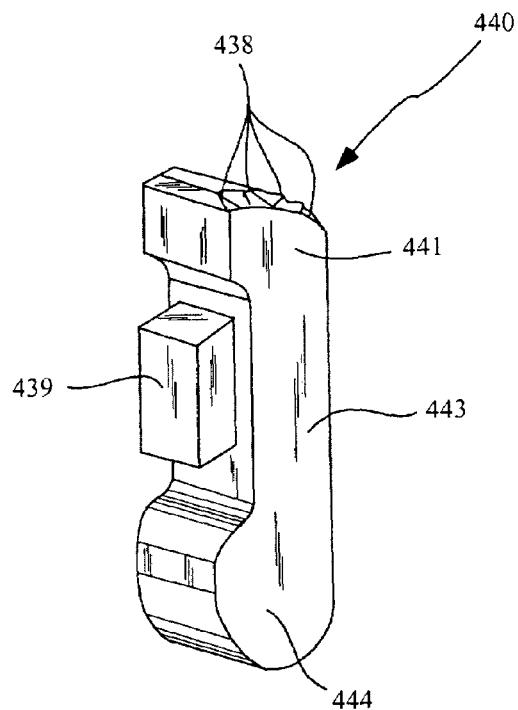
FIG. 15 is a perspective view of a preferred suture stay.

Suture locking members 440, best seen in FIG. 15, have a pivot end 444 which fits snugly within cavities 436 and 435 and a free end 441 which is biased against an inner wall of channels 431 and 432 to resist relaxation of tension member 430. Suture locking member 440 is at an angle 442 relative to the channels 431 and 432 which allows body 443 and free end 441 to flex or pivot to allow tension members 430 to be effortlessly pulled in a direction towards the outside of stabilizer feet 401 and 402 and yet prevents relaxation of tension members 430. The bias of free end 441 may be increased by including a spring or resilient material 439. One or more ridges or teeth may be provided on free end 441 to provide an improved grip against tension members 430.

Figure 16:
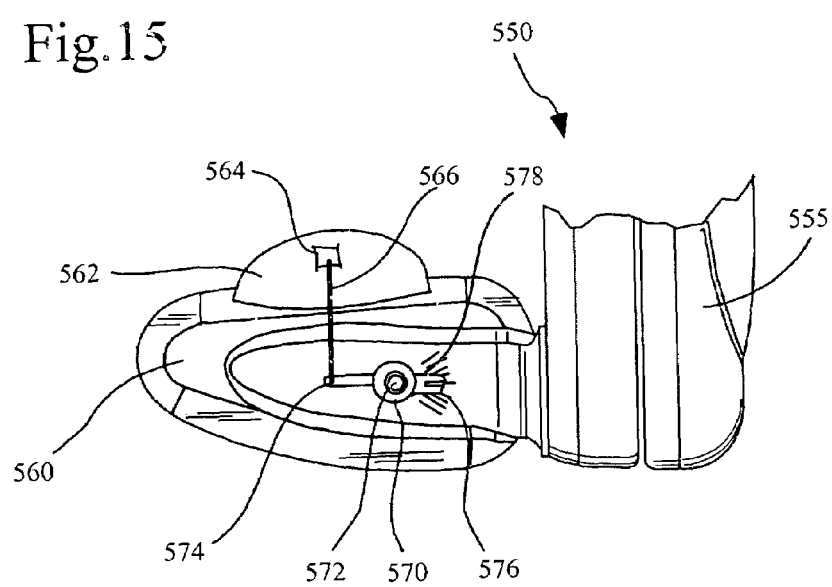
FIG. 16 is a partial top view of an alternative articulating mechanism.

Another device for articulating the moveable portions is illustrated in FIG. 16. Tissue stabilizer 550 has stabilizer foot 560 rotatably connected to manifold base 555 as discussed above. Stabilizer foot 560 has a moveable portion 562 which has a link or tension member 566 connected at attachment boss 564. Stabilizer foot 560 has a post 572 over which pivot member 570 is installed. Tension member 566 is attached to pivot member 570 at attachment point 574 such that rotation of pivot member 570 about post 572 causes tension member 566 to articulate moveable portion 562 as desired. In a preferred embodiment, pivot member 570 has an extension 576 which cooperates with detents 578 in stabilizer foot 560. Thus, pivot member 570 detents into place in predetermined increments as pivot member 570 is rotated to cause the desired articulation of moveable member 560. Thus pivot member 570 will hold a desired position within any of detents 578 for as long as required by the procedure.

In a preferred method of using a tissue stabilizer having independently rotatable feet, the tissue stabilizer is placed over the desired target coronary artery such that each stabilizer foot is positioned on opposite sides of a target vessel. The stabilizer feet are engaged against the surface of the heart using compression, negative pressure, or both to stabilize a portion of the heart under the stabilizer feet. When the stabilizer feet are constructed to engage the surface of the heart using negative pressure, one or both of the stabilizer feet may be adjusted to achieve a good seal against the heart or to cause the desired manipulation of the heart tissue. Preferably, the stabilizer feet may be independently adjusted by rotating one or both of the stabilizer feet relative to each other.

Preferably, negative pressure is also communicated to flexible members 405 and 406, causing them to become engaged with a portion of the target artery or surrounding tissue. An arteriotomy is then formed in the target artery at a desired location for anastomosing a graft or source vessel. The surgical site and arteriotomy can be manipulated using the stabilizer foot to obtain an optimal presentation. For example, the stabilizer feet can be rotated in opposite directions (one counter-clockwise and the other clockwise) to cause the tissue closest to the target artery to be pressed downward or lifted upwards. Also, the stabilizer feet can be rotated in the same direction to differentially cause upward lifting on one side of the target artery and downward pressing on the other.

The stabilizer feet may be independently adjusted using any suitable instrument. Indentations, protrusions, polygonal flats, or the like may be provided on one or both of the stabilizer feet to facilitate secure instrument engagement for positioning. If desired, the stabilizer feet may be mechanically coupled to each other by way of a gears, belts, or linkages such that movement of one stabilizer foot causes a corresponding movement in the other. Further, the stabilizer feet or coupling mechanism may be operably connected to a remote actuator by a tension wire, drive cable, linkage or the like to facilitate remote actuation of the stabilizer feet.

In addition to the overall adjustment of each stabilizer foot, one or both of the flexible members 405 and 406 can be articulated relative to the stabilizer feet. In a preferred embodiment, flexible members 405 and 406 are articulated to lift open one or both sides of the arteriotomy incised in the target artery. Preferably, flexible members 405 and 406 are articulated by pulling on tension wires attached thereto using forceps or other suitable instrument or mechanism. Once the arteriotomy has been presented as desired one or more sutures can then be safely and accurately placed. The target site may be adjusted as desired throughout the anastomosis procedure to maintain optimal presentation of the tissue to be sutured.

While certain embodiments are illustrated in the drawings and have just been described herein, it will be apparent to those skilled in the art that many modifications can be made to the embodiments without departing from the inventive concepts described. For purposes of illustration only, the principles of the present invention has been described with reference to stabilizing the heart during a coronary artery bypass procedure but may readily be applied to other types of surgical procedures on various types of tissue structures not specifically described. Many other uses are well known in the art, and the concepts described herein are equally applicable to those other uses. Further, the different components of the various exemplar embodiments described above can be combined in any desirable construction. Accordingly, the invention is not to be restricted except by the claims which follow.

What is claimed is:

1. A device for stabilizing tissue within a patient's body for performing a surgical procedure on said tissue comprising:

a base member having an interior chamber and a substantially cylindrical bore, said bore having a first end in fluid communication with said interior chamber and a second end open to the exterior of said base member;

a stabilizer foot having a substantially cylindrical fitting having a longitudinal axis, at least a portion of said fitting positioned within said bore and being rotatable within said bore about said longitudinal axis; and said stabilizer foot having a first foot portion adapted to engage a first portion of tissue and a second foot portion adapted to engage a second portion of tissue adjacent said first portion of tissue, said second foot portion being flexibly coupled to said first foot portion.

2. The device of claim 1 further comprising a tension member having a proximal end and a distal end, said distal end being operably connected to said second foot portion, whereby pulling on said proximal end causes said second foot portion to move relative to said first foot portion.

3. The device of claim 1 wherein said second foot portion comprises an elastomer.

4. The device of claim 1 wherein said second foot portion defines a vacuum space having at least one opening in fluid communication with said second portion of tissue.

5. The device of claim 4 wherein said vacuum space has a perimeter edge adapted to seal against said second portion of tissue.

6. A device for stabilizing tissue within a patient's body for performing a surgical procedure on said tissue comprising:
    a base member;
    a shaft mounted for rotation relative to said base member, said shaft having a longitudinal axis and at least one threaded portion;
    a first stabilizer foot having a first tissue engaging surface and a second stabilizer foot having a second tissue engaging surface, said first and second tissue engaging surfaces extending generally perpendicular to said longitudinal axis, at least one of said stabilizer feet being threadably engaged with said threaded portion of said shaft such that rotation of said shaft causes said at least one of said stabilizer feet to move relative to the other, and at least one of said stabilizer feet further comprising a flexible member coupled thereto, said flexible member having a vacuum chamber having at least one opening adapted to engage a portion of tissue with negative pressure.

7. The device of claim 6 wherein said shaft has a first threaded portion and a second threaded portion and said first stabilizer foot is adapted to receive and traverse along said first threaded portion and said second stabilizer foot is adapted to receive and traverse along said second threaded portion.

8. The device of claim 7 wherein said second threaded portion has threads which are opposite-handed to that of the threads of said first portion.

9. The device of claim 6 wherein said flexible member comprises an elastomer.

10. A method of stabilizing a coronary artery on a beating heart for performing a surgical procedure on the coronary artery comprising the steps of:
    providing a tissue stabilizer having at least one stabilizer foot having a first portion adapted to engage a first area on the surface of the heart adjacent said coronary artery and a second portion adapted to engage a second area on the surface of the heart, said second portion being coupled to said first portion and moveable relative to said first portion;
    engaging said first area with said first portion to substantially stabilize at least a portion of the heart;
    engaging said second area with said second portion;
    moving said second portion relative to said first portion whereby said second area of said heart is moved relative to said first area of said heart.

11. The method of claim 10 wherein said second area includes at least a portion of said coronary artery.

12. The method of claim 10 further including the step of creating an arteriotomy having a first side and a second side in said coronary artery after engaging said first area with said first portion.

13. The method of claim 12 wherein said second area includes a portion of said coronary artery adjacent said first side of said arteriotomy whereby the step of moving said second portion relative to said first portion moves said first side of said arteriotomy relative to said second side of said arteriotomy.

14. The method of claim 13 further comprising the step of placing at least one suture through a first side of said arteriotomy.

15. A device for stabilizing tissue within a patient's body for performing a surgical procedure on said tissue comprising:
    a base member having a shaft extending therefrom;
    at least one stabilizer foot extending from said base member, said stabilizer foot having a tissue engaging surface, a substantially rigid portion and a flexible portion adapted to lift a portion of the tissue engaged thereby, wherein said tissue engaging surface of said stabilizer foot is formed in part by said substantially rigid portion and in part by said flexible portion, and wherein said substantially rigid portion and said flexible portion are configured to each contact the tissue during the surgical procedure: and
    a tension member connecting with said flexible portion and configured to apply tension to drive movement of said flexible portion relative to said substantially rigid portion, wherein said flexible portion is configured to maintain engagement with the engaged tissue portion during driving movement away from the engaged tissue portion, thereby lifting the engaged tissue portion.

16. The device of claim 15, wherein said substantially rigid portion and said flexible portion together form an enclosed vacuum space having an opening adapted to engage the tissue when negative pressure is applied to said vacuum space.

17. The device of claim 16, further comprising a member positioned within said vacuum space to prevent excessive collapse of said flexible portion into said substantially rigid portion.

18. The device of claim 15, wherein a portion of said tissue engaging surface formed by said substantially rigid portion comprises projections extending therefrom and adapted to provide traction against the tissue.

19. The device of claim 15, wherein said tension member is connected proximally to said shaft.

20. The device of claim 15, further comprising a tension actuator connecting a proximal end portion of said tension member to said shaft, said tension actuator adapted to vary tension on said tension member.

21. A device for stabilizing tissue within a patient's body for performing a surgical procedure on said tissue comprising:
    a base member having a shaft extending therefrom;
    at least one stabilizer foot extending from said base member, having a tissue engaging surface, a substantially rigid portion and a flexible portion adapted to lift a portion of the tissue engaged thereby; and
    a tension member connecting with said flexible portion and configured to apply tension to drive movement of said flexible portion relative to said substantially rigid portion, wherein said flexible portion is configured to maintain engagement with the engaged tissue portion during driving movement away from the engaged tissue portion, thereby lifting the engaged tissue portion.

22. A device for stabilizing tissue within a patient's body for performing a surgical procedure on said tissue comprising:

a base member having a shaft extending therefrom;

at least one stabilizer foot extending from said base member, having a tissue engaging surface, a substantially rigid portion and a flexible portion adapted to lift a portion of the tissue engaged thereby, upon movement of the flexible portion in a direction away from the engaged tissue portion, wherein said base member comprises a threaded shaft extending therefrom, said at least one stabilizer foot being threadably engaged with said threaded shaft, such that rotation of said threaded shaft drives said at least one stabilizer foot in a direction along a longitudinal axis of said threaded shaft.

23. A device for stabilizing tissue within a patient's body for performing a surgical procedure on said tissue comprising:

a base member having a shaft extending therefrom;

at least one stabilizer foot extending from said base member, said stabilizer foot having a tissue engaging surface, a substantially rigid portion and a flexible portion adapted to lift a portion of the tissue engaged thereby, upon movement of the flexible portion in a direction away from the engaged tissue portion, wherein said tissue engaging surface of said stabilizer foot is formed in part by said substantially rigid portion and in part by said flexible portion, and wherein said substantially rigid portion and said flexible portion are configured to each contact the tissue during the surgical procedure; and a threaded shaft extending from said base member, said at least one stabilizer foot being threadably engaged with said threaded shaft, such that rotation of said threaded shaft drives said at least one stabilizer foot in a direction along a longitudinal axis of said threaded shaft.

* * * * *

UNITED STATES PATENT AND TRADEMARK OFFICE
CERTIFICATE OF CORRECTION

| | |
|---|---|
| PATENT NO. | : 7,326,177 B2 |
| APPLICATION NO. | : 10/137643 |
| DATED | : February 5, 2008 |
| INVENTOR(S) | : Williamson, IV et al. |

It is certified that error appears in the above-identified patent and that said Letters Patent is hereby corrected as shown below:

Column 3, line 49, please delete "Co" and insert therefore --to--.

Signed and Sealed this

Twenty-third Day of September, 2008

JON W. DUDAS
*Director of the United States Patent and Trademark Office*